US008962042B2

(12) United States Patent
Geng

(10) Patent No.: US 8,962,042 B2
(45) Date of Patent: Feb. 24, 2015

(54) METHODS FOR TREATING NEUROLOGICAL DISORDERS USING NUTRIENT COMPOSITIONS

(76) Inventor: Lisa Geng, Stuart, FL (US)

( * ) Notice: Subject to any disclaimer, the term of this patent is extended or adjusted under 35 U.S.C. 154(b) by 0 days.

(21) Appl. No.: 13/876,108

(22) PCT Filed: Sep. 28, 2011

(86) PCT No.: PCT/US2011/053700
§ 371 (c)(1),
(2), (4) Date: Jun. 3, 2013

(87) PCT Pub. No.: WO2012/050895
PCT Pub. Date: Apr. 19, 2012

(65) Prior Publication Data
US 2013/0330428 A1  Dec. 12, 2013

Related U.S. Application Data

(60) Provisional application No. 61/473,258, filed on Apr. 8, 2011, provisional application No. 61/387,227, filed on Sep. 28, 2010.

(51) Int. Cl.
| | | |
|---|---|---|
| A61K 36/00 | (2006.01) | |
| A61K 36/82 | (2006.01) | |
| A61K 36/328 | (2006.01) | |
| A61K 36/906 | (2006.01) | |
| A61K 36/9066 | (2006.01) | |
| A23L 1/30 | (2006.01) | |
| A23L 1/302 | (2006.01) | |
| A23L 1/304 | (2006.01) | |
| A23L 1/305 | (2006.01) | |
| A61K 36/185 | (2006.01) | |
| A61K 36/27 | (2006.01) | |
| A61K 36/47 | (2006.01) | |
| A61K 45/06 | (2006.01) | |

(52) U.S. Cl.
CPC ........... *A61K 36/9066* (2013.01); *A23L 1/3002* (2013.01); *A23L 1/3006* (2013.01); *A23L 1/302* (2013.01); *A23L 1/304* (2013.01); *A23L 1/3051* (2013.01); *A23L 1/3055* (2013.01); *A23L 1/3056* (2013.01); *A61K 36/185* (2013.01); *A61K 36/27* (2013.01); *A61K 36/328* (2013.01); *A61K 36/47* (2013.01); *A61K 36/82* (2013.01); *A61K 45/06* (2013.01); *A23V 2002/00* (2013.01)
USPC ............ 424/725; 424/729; 424/748; 424/756

(58) Field of Classification Search
None
See application file for complete search history.

(56) References Cited

U.S. PATENT DOCUMENTS

| | | | |
|---|---|---|---|
| 4,897,388 A * | 1/1990 | Malluche ...................... | 514/167 |
| 6,197,746 B1 | 3/2001 | Beck et al. | |
| 6,214,831 B1 | 4/2001 | Yokoo et al. | |
| 6,379,673 B1 | 4/2002 | Diwan et al. | |
| 6,399,114 B2 | 6/2002 | Foreman | |
| 6,733,793 B2 | 5/2004 | Pacioretty et al. | |
| 6,989,160 B2 | 1/2006 | Chauhan et al. | |
| 7,232,575 B2 | 6/2007 | Walsh et al. | |
| 7,335,651 B2 | 2/2008 | Bagchi et al. | |
| 7,456,224 B2 | 11/2008 | Chez | |
| 7,632,532 B2 | 12/2009 | McKee et al. | |
| 7,722,901 B2 | 5/2010 | Freis et al. | |
| 2003/0008048 A1 * | 1/2003 | Winston et al. ............... | 426/548 |
| 2005/0095262 A1 * | 5/2005 | Camponovo et al. ......... | 424/400 |
| 2008/0009467 A1 * | 1/2008 | Henderson ..................... | 514/129 |
| 2008/0108643 A1 | 5/2008 | Chez | |
| 2008/0145424 A1 * | 6/2008 | Ron ............................... | 424/468 |
| 2010/0143513 A1 * | 6/2010 | Lee et al. ...................... | 424/750 |

FOREIGN PATENT DOCUMENTS

| | | |
|---|---|---|
| EP | 1955602 A1 * | 8/2008 |
| JP | 01258623 | 10/1989 |
| JP | 02292208 | 12/1990 |
| JP | 2001-226274 | 8/2001 |
| WO | WO 01/17486 | 3/2001 |
| WO | WO 2005/016224 A2 * | 2/2005 |
| WO | WO 2008/103370 | 8/2008 |

OTHER PUBLICATIONS

International Search Report mailed Feb. 10, 2012 for PCT/US2011/053700 filed Sep. 28, 2011, 9 pages.
Written Opinion mailed Feb. 10, 2012 for PCT/US2011/053700 filed Sep. 28, 2011, 10 pages.
International Preliminary Report on Patentability issued Apr. 2, 2013 for PCT/US2011/053700 filed Sep. 28, 2011, 11 pages.
Morris, Claudia R., "Syndrome of Allergy, Apraxia, and Malabsorption: Characterization of a Neurodevelopmental Phenotype That Responds to Omega 3 and Vitamin E Supplementation", Alternative Therapies, Jul./Aug. 2009, pp. 34-43, vol. 15, No. 4.
Bent, Stephen et al., "Omega-3 Fatty Acids for Autistic Spectrum Disorder: A Systematic Review", J. Autism Dev Disorder, 2009, vol. 39, pp. 1145-1154, Springer.
Taylor, Barbara A., "Children with Disabilities", http://web.archive.org/web/20100603021531/http://jj smythartistry.net/ChildrenWithDisibilities.aspx, XP002667801, Jun. 3, 2012, pp. 1-6.
Anonymous: "Original Nutriiveda (NV) ingredients", http://pursuitofresearch.org/products/nutriiveda/nutriiveda-ingredients/, XP002667805, Jan. 23, 2012, 1 pg. (Summary Only).
Politi, P., et al., "Behavioral effects of omega-3 fatty acid supplementation in young adults with severe autism: an open label study", Archives of Medical Research, Oct. 1, 2008, vol. 39, No. 7, pp. 682-685.
Anonymous: "Nutriiveda", http://web.archive.org/web20100901071815/http://zriiproduct.com/nutriiveda_ingredients.html, XP002667804, Sep. 1, 2010, 1 pg.
Diagnostic & Statistical Manual of Mental Disorders (DSM-IV-TR), American Psychiatric Association (APA) ,2000.
Agin, M., et al., "The Late Talker—What to do if your child isn't Talking Yet", May 2004, St. Martin's Press.
Mosby's Medical Dictionary, $5^{th}$ edition 1998, pp. 361 and 1008.
Erasmus, Udo., "Fats and Oils", 1986, p. 263, Alive Books, Vancouver.
Fan, Yang-Yi, et al., "Importance of Dietary ã-Linolenic Acid in Human health and Nutrition", Journal of Nutrition, Sep. 9, 1998, vol. 128, No. 9, pp. 1411-1414.

(Continued)

*Primary Examiner* — Qiuwen Mi
(74) *Attorney, Agent, or Firm* — Feldman Gale PA; Walter C. Frank

(57) ABSTRACT

Nutrient compositions comprising botanical extracts and methods of their use for treating, inter alia, autism or apraxia and/or ameliorating one or more symptoms thereof are disclosed. The use of such compositions for enhancing cognitive function and/or one or more aspects thereof, or for treating stroke or seizures and/or ameliorating one or more symptoms thereof are also disclosed.

29 Claims, No Drawings

(56) References Cited

OTHER PUBLICATIONS

Belch et al., "Evening primrose oil and borage oil in rheumatologic conditions", American Journal of Clinical Nutrition, Jan. 2000, vol. 71, No. 1, pp. 352S-356S.

Irwin, "Primary Observation (Irwin) Test", Psychopharmacologia, vol. 13, pp. 222-257, 1966.

Lemaire et al., Psychopharmacology, 1994, vol. 15, pp. 435-440.

Brown et al., J. Pharmacol. Exp. Ther., 1953, vol. 107, pp. 273-283.

Jennifha et al., "Nuteiiveda??", Apr. 26, 2010, XP002667802, Retrieved from Internet, URL:http://www.autismweb.com/form/viewtopic.php?f=4&t=22989&view=next.

Geng, Lisa, "You may have heard of nutriiveda", Mar. 10, 2010, XP002667803, Retrieved from Internet: URL:http://health.groups.yahoo.com/group/Autism-Mercury/message276793.

Geng, Lisa, "Cherub Blog Nutriiveda (NV) Startling PreClinical Research for Therapeutic Use", Jan. 23, 2012, XP002667806, Retrieved from Intranet: URL:http://www.cherubfoundation.org/2011/nutriiveda-nv-startling-preclinical-research-for-therapeutic-use/.

Anonymus, Zrii launches Nutriiveda Achieve: the latest, all natural breakthrough in weight loss and weight management, May 30, 2011, XP002667807, Retrieved from Internet: URL:http://www.prweb.com/releases/2011/5/prweb8487755.htm.

Amminger et al., "Omega-3 Fatty Acids Supplementation in Children with Autism: A Double-blind Randomized, Placebo-controlled Pilot Study", Biological Psychiatry, Feb. 2007, vol. 61, No. 4, Elsevier Science, New York, New York.

Johnson, Cynthia R., "Polyunsaturated Fatty Acid Supplementation in Young Children with Autism", Journal of Developmental and Physical Disabilities, Oct. 13, 2009, vol. 22, No. 1, pp. 1-10, Kluwer Academic Publishers—Plenum Publishers, NE.

http://pursuitofresearch.org/2010/11/01/the-science-nutrition-and-special-needs/.

http://planetthrive.com/2010/01/unravelling-the-mystery-of-autism/.

Bharata Bhaisajya Ratnakara, Pages(s) being submitted—07 (Pg.No. 04-10), ( Ref.pg. no.of publication:634 ), Aug. 1999, B. Jain Publishers, New Delhi, India.

Ali Ibn-e-Abbaas Majoosi, Kaamil-al-Sena'ah, Part II, Pages(s) being submitted—06 (Pg.No. 11-16), ( Ref.pg. no.of publication:577 ), 2005, Central Council for Research in Unani Medicine, 61-65 Institutional Area, Janak Puri, New Delhi-58, India.

Tisatacharya, Cikitsa kalika, Page(s) being submitted—07 (Pg.No. 17-23), ( Ref.pg. no.of publication:153 ), First Edition, 1987, Chaukhambha Surbharati Prakashan, Varanasi, India.

\* cited by examiner

METHODS FOR TREATING NEUROLOGICAL DISORDERS USING NUTRIENT COMPOSITIONS

CROSS REFERENCE TO RELATED APPLICATIONS

This application is a national stage application of PCT/US2011/053700 filed Sep. 28, 2011, which claims the benefit of U.S. Provisional Application No. 61/387,227 filed Sep. 28, 2010 and U.S. Provisional Application No. 61/473,258 filed Apr. 8, 2011, the disclosures of which are hereby incorporated herein by reference in their entireties.

FIELD OF THE INVENTION

The present invention relates to methods for treating, inter alia, autism or apraxia and/or ameliorating one or more symptoms thereof.

BACKGROUND OF THE INVENTION

Autism is a complex developmental disorder that interferes with, among other things, the normal development of the brain in the areas of social interaction, imagination, reasoning ability, cognition, and communication skills. It typically appears during the first three years of life and is the result of a neurological disorder which affects the functioning of the brain. Typically, autistic children and adults have difficulties in verbal and non-verbal communication, social interactions, and leisure or play activities. Formerly a rare disorder, autism has increased in the last decade by 300% to 500% in the United States and many other countries. Clearly, a means of prevention and/or treatment of what is now an epidemic are needed.

According to the Autism Society of America (hereinafter the "ASA"), autism is generally characterized as one of five disorders coming under the umbrella of Pervasive Developmental Disorders (PDD), a category of neurological disorders characterized by severe and pervasive impairment in several areas of development, including social interaction and communications skills (DSM-IV-TR). The five disorders under PDD are Autistic Disorder, Asperger's Disorder, Childhood Disintegrative Disorder (CDD), Rett's Disorder, and PDD-Not Otherwise Specified (PDD-NOS). Specific diagnostic criteria for each of these disorders can be found in the Diagnostic & Statistical Manual of Mental Disorders (DSM-IV-TR) as distributed by the American Psychiatric Association (APA).

The most common of the Pervasive Developmental Disorders, autism spectrum disorders affect an estimated 1 in approximately 110 births on average according to a 2009 study by the Center for Disease Control. Indeed, as of 2003-2004, as many as 1.5 million Americans are believed to have some form of autism. Such a number is on the rise inasmuch as, based on statistics from the U.S. Department of Education and other governmental agencies, autism is growing at a rate of 10-17 percent per year. At these rates, the ASA estimates that the prevalence of autism could easily reach 4 million Americans in the next decade.

The overall incidence of autism is, for the most part, globally consistent. Indeed, autism knows no racial, ethnic, or social boundaries, and family income, lifestyle, and educational levels do not affect the chance of autism's occurrence. However, it has been found to be four times more prevalent in boys than girls.

Although autism is defined by a certain set of behaviors, it is a spectrum disorder in that its symptoms and characteristics can be present in a wide variety of combinations, from mild to severe. Therefore, autistic children and adults can exhibit any combination of the behaviors in any degree of severity. Two individuals, both with the same diagnosis, may have varying skills and display very different actions.

Indeed, every person with autism is an individual, and like all individuals, each has a unique personality and combination of characteristics. Those only mildly affected may exhibit slight delays in language or communication and may face greater challenges in social interactions. For example, one may have difficulty initiating and/or maintaining a conversation. Communication by autistic children or adults is often displayed as talking at others (for example, a monologue on a favorite subject that continues despite attempts by others to interject comments).

Autism requires those affected by it to process and respond to information in unique ways. At times, aggressive and/or self-injurious behavior may exist. The following traits, as identified by the ASA, may also be present in persons with autism: Insistence on sameness or resistance to change; Difficulty in expressing needs; (i.e. uses gestures or pointing instead of words); Repeating words or phrases in place of normal, responsive language; laughing, crying, showing distress for reasons not apparent to others; prefers to be alone or aloof manner; tantrums; difficulty in mixing with others; may not want to cuddle or be cuddled; little or no eye contact; unresponsive to normal teaching methods; sustained odd play; spins objects; inappropriate attachments to objects; apparent over-sensitivity or under-sensitivity to pain; no real fears of danger; noticeable physical over-activity or extreme under-activity; uneven gross/fine motor skills; and/or not responsive to verbal cues (i.e. acts as if deaf although hearing tests in normal range).

For most people, our senses help us to understand what we are experiencing. For example, our senses of touch, smell, sound, and taste collaborate to give us a full experience of eating a ripe apple: the feel of the smooth skin as we pick it up, its sweet smell as we move it to our mouth, the crunch of the fruit being bitten into, and the juices running down our face as we enjoy the bite. For individuals with autism, however, sensory integration problems are common. In particular, their senses may be either over- or under-active. The fuzz of a kiwi may actually be experienced as painful; a sweet, fruity smell may cause a gagging reflex. Some children or adults with autism are particularly sensitive to sound, so that even the most ordinary daily noises are painful. Many professionals feel that some of the typical autism behaviors are actually a result of sensory integration difficulties.

While there is no known single known cause for autism, it is generally accepted that it is caused by abnormalities in brain structure or function. The shape and structure of the brain in autistic versus non-autistic children show differences when brain scans are viewed. Currently the link between heredity, genetics and medical problems are being investigated by researchers, as well as a number of other theories. The theory of a genetic basis of the disorder is supported by the fact that, in many families, there appears to be a pattern of autism or related disabilities. While no one gene has been identified as causing autism, researchers are searching for irregular segments of genetic code that autistic children may have inherited. While researchers have not yet identified a single "trigger" that causes autism to develop, it also appears that some children are born with a susceptibility to autism.

Other researchers are investigating the possibility that under certain conditions, a cluster of unstable genes may interfere with brain development resulting in autism. Still other researchers are investigating problems during pregnancy or delivery as well as environmental factors such as viral infections, metabolic imbalances, and exposure to environmental chemicals.

According to the ASA, autism tends to occur more frequently than expected among individuals who have certain medical conditions, including Fragile X syndrome, tuberous sclerosis, congenital rubella syndrome, and untreated phenylketonuria (PKU). Some harmful substances ingested during pregnancy also have been associated with an increased risk of autism. Early in 2002, The Agency for Toxic Substances and Disease Registry (ATSDR) prepared a literature review of hazardous chemical exposures and autism found no compelling evidence for an association; however, there was very limited research and more needs to be done.

Notwithstanding the foregoing, and to the best of Applicant's knowledge, there is no cure for autism. There are, however, a number of medications, developed for other conditions, which have been found to be somewhat helpful in treating a limited number of the symptoms and behaviors frequently found in individuals with autism, such as hyperactivity, impulsivity, attention difficulties, and anxiety. Examples of medications used to treat symptoms associated with autism include: Serotonin re-uptake inhibitors (e.g. clomipramine (Anafranil), fluvoxamine (Luvox) and fluoxetine (Prozac)) which have been effective in treating depression, obsessive-compulsive behaviors, and anxiety that are sometimes present in autism. Studies have shown that they may reduce the frequency and intensity of repetitive behaviors, and may decrease irritability, tantrums and aggressive behavior. Some children have shown improvements in eye contact and responsiveness. Other drugs, such as Elavil, Wellbutrin, Valium, Ativan and Xanax, require more studies to be done but may have a role in reducing behavioral symptoms.

Over the past 35 years, the most widely studied psychopharmacologic agents in autism have been anti-psychotic medications. Originally developed for treating schizophrenia, these drugs have been found to decrease hyperactivity, stereotypic behaviors, withdrawal and aggression in autistic children. Four that have been approved by the FDA are clozapine (Clozaril), risperidone (Risperdal), olanzapine (Zyprexa) and quetiapine (Seroquel). However, only risperidone has been investigated in a controlled study of adults with autism. Unfortunately, like the antidepressants, these drugs all have adverse side effects, including, but not limited to, sedation.

Stimulants, such as Ritalin, Adderall, and Dexedrine, used to treat hyperactivity in children with ADHD have also been prescribed for children with autism. Although few studies have been done, they may increase focus, and decrease impulsivity and hyperactivity in autism, particularly in higher-functioning children. Unfortunately, adverse behavioral side effects are often observed.

While many of the above-identified medications do appear to be somewhat helpful in treating a limited number of the symptoms and behaviors frequently found in individuals with autism, a wide variety of side effects are associated with such medications.

Apraxia is another of the neurological disorders or conditions that effects brain function. It is typically defined as the inability to carry out useful or skilled acts while motor power and mental capacity remain intact. Apraxia is generally understood to usually be caused by damage to specific areas of the cerebrum. Apraxia may be further divided into kinetic, or motor, apraxia, ideational apraxia, and constructional apraxia. Kinetic apraxia affects the upper extremities so that the individual cannot carry out fine motor acts, such as turning a key in a lock, even though there is no muscle weakness. Ideational apraxia is characterized by the inability to formulate a plan of action and is usually caused by a lesion of the cerebral cortex. This may manifest itself as a plan is never fully organized, with the part that is organized not remembered long enough to be performed. Alternatively, portions of an act may be completed in an improper sequence. For example, an individual may strike a match to light a campfire but then hold the match until it burns his fingers. Ideokinetic apraxia may be caused by an interruption of impulses in the association tracts of the nervous system, such that there is no coordination between ideation and motor activity. An affected individual will complain, for example, that he cannot use his hand, but then he will slap a mosquito with it. People with ideokinetic apraxia are unable to perform certain acts (e.g., whistling or making a first) upon command but are able to do so automatically. Ideokinetic apraxia is usually caused by a lesion in the supramarginal gyrus of the cerebral cortex. Constructional apraxia, typically caused by a lesion in the right cerebral hemisphere, is the inability to construct elements in the correct fashion to form a meaningful whole—e.g., being unable to build a structure with blocks or to copy a design.

Various disorders and diseases exist that affect cognitive function. Cognitive function may be generally described as including at least three different components: attention, learning, and memory. Each of these components and their respective levels affect the overall level of a subject's cognitive ability. For instance, while Alzheimer's Disease patients suffer from a loss of overall cognition and thus deterioration of each of these characteristics, it is the loss of memory that is most often associated with the disease. In other diseases, patients suffer from cognitive dysfunction or impairment that is more predominately associated with different characteristics of cognition. Other conditions include general dementias associated with other neurological diseases, aging, and treatment of conditions that can cause deleterious effects on mental capacity, such as cancer treatments, stroke/ischemia, and mental retardation.

Cognitive dysfunction creates a variety of problems for today's society. Therefore, scientists have made efforts to develop cognitive enhancers or cognition activators. The cognition enhancers or activators that have been developed are generally classified to include nootropics, vasodilators, metabolic enhancers, psychostimulants, cholinergic agents, biogenic amine drugs, and neuropeptides.

U.S. Pat. No. 6,399,114 discloses certain compositions for treating nervous system disorders including autism, ADD, ADHD, hyperactivity disorder and depression.

U.S. Pat. No. 7,456,224 discloses methods for treating autism comprising the step of administering an effective amount of a medicament characterized as a NMDA-receptor antagonist or a pharmaceutically acceptable salt thereof.

U.S. Pat. No. 7,335,651 discloses methods for promoting healthy body weight and improving a number of related physiological factors.

U.S. Pat. No. 7,232,575 discloses certain nutrient supplements comprising minerals, vitamins, amino acids, and agents capable of delivering cysteine in vivo and methods of treating autism involving administration of the nutrient supplements.

U.S. Pat. No. 7,632,532 discloses certain delivery systems for nutraceuticals using a low caloric chocolate base for containing one or more nutraceuticals.

*Gymnema sylvestre* (Retz.) R. Br. ex Schult (belonging to the family Asclepiadaceae) is a woody climbing plant that grows in the tropical forests of central and southern India. The leaves are used in herbal medicine preparations. It is an Ayurvedic herb, and used to be known as "destroyer of sugar", because in ancient times Ayurvedic physicians observed that chewing a few leaves of *Gymnema sylvestre* suppressed the taste of sugar. Today it is used all over India for controlling blood sugar (Baskaran K., Kizar Ahamath B., Radha Shanmugasundaram K., Shanmugasundaram E. R., Antidiabetic effect of a leaf extract from *Gymnema sylvestre* in non-insulin-dependent diabetes mellitus patients, J Ethnopharmacol, volume 30, pages 295 to 300, 1990).

*Gymnema sylvestre* is stomachic, diuretic, refrigerant, astringent, and tonic. It has been found to increase urine output and reduce hyperglycemia in both animal and human studies.

U.S. Pat. No. 6,379,673 discloses an herbal formulation for therapeutic and cosmetic applications for the treatment of general skin disorders that contains an aqueous extract of *Gymnema sylvestre*.

U.S. Pat. No. 7,632,532 discloses certain systems and methods for oral administration of various nutraceuticals such as plant concentrates, particularly in confectionary or chocolate matrices utilizing a novel sweetening composition.

JP-A 2001 226 274 discloses a lipase inhibitor that comprises a crude drug or its extract such as guava leaf (*Psidium guajava*), hop (*Humulus lupulus*), *Apocynum venetum* leaf, *Gymnema* leaf (*Gymnema sylvestre*), and/or *Gardenia fructus* (*Gardenia jasminoides* var. *grandiflora*). The lipase inhibitor according to JP-A 2001 226 274 has the following functions: anorectic, antidiabetic, antilipemic and hypotensive.

WO 01/17486 discloses a method for the cosmetic treatment of skin impairments and baldness by applying deanol or derivatives thereof (deanol is also known as dimethylaminoethanol).

JP-A 2292208 discloses a cosmetic preparation that contains substances obtained from leaves of *Gymnema sylvestre*, *Zizyphus jujuba*, bark and peelings of *Malus pumila* and further substances.

JP-A 02292208 discloses a cosmetic preparation that contains substances obtained from leaves of *Gymnema sylvestre*. The substances are obtained by extraction. The solvent used for extraction is water, alcohol, or mixtures of water and alcohol. The cosmetic preparation according to JP-A 02292208 can be used for the treatment of blotches and freckles.

JP-A 01258623 discloses a composition that stimulates hair growth and blood circulation and prevents baldness. It contains chitin and chitosan in combination with hydrolysing enzymes, organic acids, and substances of *Gymnema sylvestre* and Isagol (hemicellulose of Plantag).

It has now been surprisingly discovered that administering an effective amount of certain nutrient compositions appears to substantially improve frontal executive functions associated with apraxia, autism, traumatic brain injury, global delays, and/or ADHD, including, but not limited to, speech expression and decreased perseveration. Furthermore, administering such nutrient compositions has not been shown to cause side effects associated with medications previously used to treat the symptoms of apraxia, autism, traumatic brain injury, global delays, and ADHD. The present invention is directed to these, as well as other important ends.

SUMMARY OF THE INVENTION

Accordingly, the present invention is directed, in part, to methods for treating apraxia, autism, speech impairments, traumatic brain injury, seizure disorders, epilepsy, global delays, or ADHD, or methods for ameliorating one or more of the symptoms thereof.

In certain embodiments, the present invention provides methods for treating apraxia, autism, speech impairments, traumatic brain injury, seizure disorders, epilepsy, global delays, or ADHD, comprising administering to a patient in need thereof a nutrient composition that ameliorates one or more symptoms of apraxia, autism, speech impairments, traumatic brain injury, seizure disorders, epilepsy, global delays, or ADHD, said nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

The present invention is also directed in part to methods for treating apraxia, autism, speech impairments, traumatic brain injury, seizure disorders, epilepsy, global delays, or ADHD, comprising administering to a patient in need thereof a nutrient composition that ameliorates one or more symptoms of apraxia, autism, speech impairments, traumatic brain injury, seizure disorders, epilepsy, global delays, or ADHD, said nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

In certain other embodiments, the present invention provides nutrient compositions useful for treating apraxia, autism, speech impairments, traumatic brain injury, seizure disorders, epilepsy, global delays, or ADHD, comprising administering to a patient in need thereof a nutrient composition that ameliorates one or more symptoms of apraxia, autism, speech impairments, traumatic brain injury, seizure disorders, epilepsy, global delays, or ADHD, said nutrient composition comprising:

an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

In one aspect, the invention is directed to methods for enhancing cognitive function, comprising the step of:

administering to a patient in need thereof a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

In one aspect, the invention is directed to methods for enhancing cognitive function, comprising the step of:

administering to a patient in need thereof a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

In one aspect, the invention is directed to methods for treating stroke, comprising the step of:

administering to a patient in need thereof a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

In one aspect, the invention is directed to methods for treating stroke, comprising the step of:

administering to a patient in need thereof a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

DETAILED DESCRIPTION OF ILLUSTRATIVE EMBODIMENTS

As employed above and throughout the disclosure, the following terms, unless otherwise indicated, shall be understood to have the following meanings.

The term "autism" as used herein includes those disorders (i.e., classical autism and autism spectrum), and pervasive developmental disorder (PDD) (i.e., with autistic tendencies) as identified by the criteria set forth in the American Psychiatric Association's Diagnostic and Statistic Manual (DSM IV, or a later version of DSM). Pervasive Developmental Disorders (as described in DSM IV) are characterized by severe and pervasive impairment in several areas of development: reciprocal social interaction skills, communication skills, or the presence of stereotyped behavior, interests, and activities. The qualitative impairments that define these conditions are distinctly deviant relative to the individual's developmental level or mental age. Pervasive Developmental Disorders include Autistic Disorder, Rett's Disorder, Childhood Disintegrative Disorder, Asperger's Disorder, and Pervasive Developmental Disorder Not Otherwise Specified. These disorders are usually evident in the first years of life and are often associated with some degree of mental retardation. Furthermore, although terms like "psychosis" and "childhood schizophrenia" were once used to refer to individuals with these conditions, there is considerable evidence that the Pervasive Developmental Disorders are distinct from schizophrenia.

The essential features of Autistic Disorder (described in DSM IV, Section 299.00) are the presence of markedly abnormal or impaired development in social interaction and communication and a markedly restricted repertoire of activity and interests. Manifestations of the disorder vary greatly depending on the developmental level and chronological age of the individual. Autistic Disorder is sometimes referred to as early infantile autism, childhood autism, or Kanner's autism. Early epidemiological studies suggested rates of Autistic Disorder of 2-5 cases per 10,000 individuals (with a greater frequency in males), but much higher rates have been reported recently. By definition, the onset of Autistic Disorder is prior to age 3 years.

The essential feature of Rett's Disorder (described in DSM IV, Section 299.80) is the development of multiple specific deficits following a period of normal functioning after birth. Rett's Disorder is typically associated with Severe or Profound Mental Retardation, and has been diagnosed only in females.

The essential feature of Childhood Disintegrative Disorder (described in DSM IV, Section 299.10) is a marked regression in multiple areas of functioning following a period of at least 2 years of apparently normal development. Childhood Disintegrative Disorder is usually associated with Severe Mental Retardation, and has also been termed Heller's syndrome, dementia infantilis, or disintegrative psychosis.

The essential features of Asperger's Disorder (described in DSM IV, Section 299.80) are severe and sustained impairment in social interaction and the development of restricted, repetitive patterns of behavior, interests, and activities. The disturbance must cause clinically significant impairment in social, occupational, or other important areas of functioning. In contrast to Autistic Disorder, there are no clinically significant delays in language (e.g., single words are used by those that are 2 years of age, communicative phrases are used by those that are 3 years of age). In addition, there are no clinically significant delays in cognitive development or in the development of age-appropriate self-help skills, adaptive behavior (other than in social interaction), and curiosity about the environment in childhood.

The category Pervasive Developmental Disorder Not Otherwise Specified (including Atypical Autism) (described in DSM IV, Section 299.80) is applied when there is a severe and pervasive impairment in the development of reciprocal social interaction or verbal and nonverbal communication skills, or when stereotyped behavior, interests, and activities are present, but the criteria are not met for a specific Pervasive Developmental Disorder, Schizophrenia, Schizotypal Personality Disorder, or Avoidant Personality Disorder.

Autism is generally understood as a group of related disorders, where people diagnosed with the condition experience its symptoms to a greater or lesser extent. At the severe end of the spectrum is low-functioning autism, which can cause extensive impairments in all areas of development. Usually, low functioning (or severely) autistic children have little or no language, some degree of mental challenges, little awareness of other people and expectations. Autistic symptoms such as gestures, rituals and many other odd behaviors are visibly apparent in lower functioning children. Self injurious behavior is much more common in low-functioning autistics than in their high-functioning peers. Individuals who are labeled as having a severe autism with cognitive impairment are individuals who have greater difficulty with social skills, and academic performance. They often have few readily known and/or socially appropriate means for communicating with others. Children with severe autism may also engage in more sensory-related activities such as hand flapping, spinning, or rocking. People with severe autism usually do not speak, often do not understand receptive language, do not care nor do they wish to engage in conversation unless it is absolutely necessary and it is extremely limited due to the lack of speech, do not respond well to behavioral therapy, and do not show a great deal of improvement. For children with low functioning autism being mentally challenge is common, epilepsy is common, and other disorders may be present as well. They do not express emotions (except anger) and whether they experience those emotions is unknown due to their inability to communicate. Some of the more common traits of those with severe autism include hand-wringing, appearance of poorly coordinated manner of walking/stepping, severely impaired expressive and receptive language development, lack of or infrequent initiation, lack of usual nonverbal gestures (i.e., pointing, head shake, nod), inability to control improper behavior, avoidance of eye contact or use of eye contact in odd ways, a preference to be alone, an iInability to imitate (body movement, vocal, motor), a propensity to engage in rhythmic body movements such as rocking, pacing, hand flapping, toe walking, spinning, either over- and under-sensitivity to sound, smell, touch, visual stimulus and pain, unusual displays of emotion such as giggling or weeping for no apparent reason, impulsivity, aggressive and/or self-injurious behavior.

As used herein, the term "stimming" refers to self-stimulating behaviors, i.e., stereotyped or repetitive movements or posturing of the body. They include mannerisms of the hands (such as handflapping, finger twisting or flicking, rubbing, or wringing hands), body (such as rocking, swaying, or pacing), and odd posturing (such as posturing of the fingers, hands, or arms). Stimming may involve objects such as tossing string in the air or twisting pieces of lint. These mannerisms may appear not to have any meaning or function, although they may have significance for the child, such as providing sensory stimulation (also referred to as self-stimulating behavior), communicating to avoid demands, or request a desired object or attention, or soothing when wary or anxious. These repetitive mannerisms are common in children with autism spectrum disorders.

The term "apraxia" as used herein is a neurological motor speech impairment—a breakdown in the transmission of messages from the brain to the muscles in the jaw, cheeks, lips, tongue, and palate. There is no obvious weakness in these muscles and the patient may well be able to happily move them when not trying to speak. A patient with apraxia knows what he wants to say, but has an impairment in the signal from the brain to the mouth. Further detail on apraxia, autism, and/or related conditions such as oral apraxia, hypotonia, sensory integration dysfunction and the like are disclosed in "The Late Talker-What to do if your child isn't Talking Yet" by Marilyn Agin M D, Lisa Geng, and Malcolm J. Nicholl, St Martin's Press May 2003. As used herein. The terms "oral apraxia" and "verbal apraxia" are both neurologically based motor planning impairments that inhibit an individual's ability to perform task on command. Verbal apraxia affects the individual's expressive ability on command. Classic symptoms noted for verbal apraxia include the ability or lack thereof to say a word on command. This may be further accentuated by the length and/or complexity of the utterance.

Oral apraxia affects an individual's ability facially communicate such as to smile, make facial expressions, and the like (e.g., blow kisses or bubbles). Other symptoms may include "blank" looks in children which affect the way they are viewed by others. Individuals with oral apraxia also have an inability to lick food off their lips, and will typically use their finger instead.

An individual may have verbal without oral apraxia. However, an individual diagnosed with oral apraxia will likely later be diagnosed with verbal apraxia as well. Today most that are diagnosed with oral and or verbal apraxia present mutlifaceted symptoms and also have sensory integration dysfunction, hypotonia (typically mild) and motor planning impairments in the body, also referred to as global or limb apraxia, or called "dyspraxia" in the UK. In the US, the diagnosis term apraxia and dyspraxia are used interchangeably however.

"Side effect" refers to a consequence other than the one(s) for which an agent or measure is used, as the adverse effects produced by a drug, especially on a tissue or organ system other than the one sought to be benefited by its administration.

"Effective amount" refers to an amount of a nutrient composition as described herein that may be therapeutically effective to treat the symptoms of particular disease, disorder, condition, or side effect. Such diseases, disorders, conditions, and side effects include, but are not limited to, those pathological conditions associated with the treatment of apraxia, autism, traumatic brain injury, global delays, or ADHD. Thus, for example, the term "effective amount", when used in connection with nutrient compositions of the invention, for the treatment of apraxia, autism, traumatic brain injury, global delays, ADHD, refers to the treatment of one or more of the symptoms related to apraxia, autism, traumatic brain injury, global delays, or ADHD, such as for example lowered ability or capability with regard to speech articulation, complexity and sophistication of sentence structure, written and spoken language comprehension and use, word, recall memory and/or learning capabilities, fine and gross motor skills including also multi tasking, sense of humor, awareness of surroundings, use of facial expressions especially as non-verbal cues, task focus, social communication skills, and or seizure instances. The term "effective amount", when used in connection with nutrient compositions of the invention, for the treatment of stroke, refers to the treatment of one or more of the symptoms related to the symptoms of stroke, such as for example, hemiplegia and muscle weakness of the face, numbness, reduction in sensory or vibratory sensation, initial flaccidity (hypotonicity), replaced by spasticity (hypertonicity), hyperreflexia, and obligatory synergies, if one of the three prominent central nervous system pathways—the spinothalamic tract, corticospinal tract, or dorsal column (medial lemniscus), is affected. A stroke affecting the brain stem and brain therefore can produce symptoms relating to deficits in one or more of the twelve cranial nerves, including such symptoms as altered smell, taste, hearing, or vision (total or partial), drooping of eyelid (ptosis) and weakness of ocular muscles, decreased reflexes: gag, swallow, pupil reactivity to light, decreased sensation and muscle weakness of the face, balance problems and nystagmus, altered breathing and heart rate, weakness in sternocleidomastoid muscle with inability to turn head to one side, and weakness in tongue (inability to protrude and/or move from side to side). If the cerebral cortex is involved, the CNS pathways can again be affected, but also may produce one or more of the following symptoms: aphasia (difficulty with verbal expression, auditory comprehension, reading and/or writing Broca's or Wernicke's area typically involved), dysarthria (motor speech disorder resulting from neurological injury), apraxia (altered voluntary movements), visual field defect, memory deficits (involvement of temporal lobe), hemineglect (involvement of parietal lobe), disorganized thinking, confusion, hypersexual gestures (with involvement of frontal lobe), and anosognosia (persistent denial of the existence of a, usually stroke-related, deficit). If the cerebellum is involved, the patient may have one or more of the following symptoms: trouble walking, altered movement coordination, vertigo and/or disequilibrium. The term "effective amount", when used in connection with nutrient compositions of the invention, for the enhancement of cognitive function, refers to the enhancement of one or more of the aspects of cognitive functions, such as for example, attention, learning, and memory, particularly memory. The characteristics of cognitive function may also be viewed in terms of their right and left brained aspects. For example, description of left brain function may employ terms such as logical, sequential, rational, analytical, or objective thought, or those brain processes involving looking at parts of the whole that are being observed or studied. Examples include concrete thought, focus and academic achievements. Description of right brain function characteristics, on the other hand, may employ terms such as random/intuitive, holistic, synthesizing, subjective, or those brain processes involving looking at the whole that is being observed or studied. Examples include imagination or creativity. Enhancement in cognitive function may include some or all of right brain or left brain characteristics, or some or all of both. The cognitive function enhancements relating to focus may include aspects of improved attention to surroundings, or absorption of details relating to the thing studied, or both. Improvement in cognitive function may also appear and/or be recognized by improvements in tested IQ of a patient.

"Stroke" refers to a condition due to the lack of oxygen to the brain. Strokes can be classified into two major categories: ischemic and hemorrhagic. Ischemic strokes are those that are caused by interruption of the blood supply, while hemorrhagic strokes are the ones which result from rupture of a blood vessel or an abnormal vascular structure. Brain tissue ceases to function if deprived of oxygen for more than 60 to 90 seconds and after approximately three hours, will suffer irreversible injury possibly leading to death of the tissue, i.e., infarction. Symptoms of the occurrence of a stroke depend on the area of the brain and/or CNS affected. In most cases, the symptoms affect only one side of the body (unilateral). Depending on the part of the brain affected, the defect in the brain is usually on the opposite side of the body. However, since these pathways also travel in the spinal cord and any lesion there can also produce these symptoms, the presence of any one of these symptoms does not necessarily indicate a stroke.

"Dosage unit" refers to physically discrete units suited as unitary dosages for the particular individual to be treated. Each unit may contain a predetermined quantity of active extract (s) calculated to produce the desired therapeutic effect (s) in association with the required pharmaceutical or edible food carrier. The specification for the dosage unit forms of the invention may be dictated by (a) the unique characteristics of the active ingredients in the nutrient compositions and the particular therapeutic effect(s) to be achieved, and (b) the limitations inherent in the art of compounding such nutrient compositions. In certain preferred embodiments, each unit may contain a predetermined quantity of active extract(s), omega 3 fatty acid(s) and/or agent(s) for the treatment of apraxia, autism, speech impairments, traumatic brain injury, seizure disorders, epilepsy, global delays, or ADHD or any mixture thereof calculated to produce the desired therapeutic effect(s) in association with an optional carrier. The specification for the dosage unit forms of the invention may be dictated by (a) the unique characteristics of the active extract (s), omega 3 fatty acid(s) and/or agent(s) for the treatment of apraxia, autism, speech impairments, traumatic brain injury, seizure disorders, epilepsy, global delays, or ADHD or any mixture thereof and the particular therapeutic effect(s) to be achieved, and (b) the limitations inherent in the art of compounding such active extract(s), omega 3 fatty acid(s) and/or agent(s) for the treatment of apraxia, autism, speech impairments, traumatic brain injury, seizure disorders, epilepsy, global delays, or ADHD or any mixture thereof.

"Patient" refers to animals, including mammals, preferably humans.

The terms "treat", "treatment" or "treating", as used herein, generally refer to palliative (e.g., therapeutic), preventative (e.g., prophylactic), inhibitory and/or curative treatment. Preferably, the terms "treat", "treatment" and/or "treating" refer to palliative, inhibitory, and/or curative treatment, with palliative and inhibitory treatment being more preferred. In particularly preferred embodiments, the terms "treat", "treatment" or "treating" refer to palliative treatment.

"In combination with", refers, in certain embodiments, to the concurrent administration to a patient of a nutrient composition of the invention including, for example, an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and one or more additional agents including, for example, an omega 3 fatty acid, or an agent for the treatment of and mixtures thereof), preferably an effective amount of an omega 3 fatty acid or pharmaceutically acceptable or food grade acceptable derivative thereof. When administered in combination, each component may be administered at the same time or sequentially in any order at different points in time. Thus, each component may be administered separately but sufficiently closely in time so as to provide the desired therapeutic effect.

Combinations of components and/or variables are permissible only if such combinations result in stable compositions.

The invention relates to nutrient compositions containing these botanical extracts and methods for their pharmaceutical use. In some embodiments, the compositions of the present invention may be useful, inter alia, in methods for treating apraxia, autism, traumatic brain injury, global delays, or ADHD or any of the symptoms thereof. In other embodiments, the compositions of the present invention may be useful, inter alia, in methods for treating learning disabilities including, for example, ADHD. In still other embodiments, the compositions of the present invention may be useful, inter alia, in methods for treating neurologically based multifaceted communication and/or behavioral impairments. In certain embodiments, the compositions of the present invention may be useful, inter alia, for treating stroke or any of the symptoms associated with stroke. In yet other embodiments, the compositions of the present invention may be useful, inter alia, for enhancing cognitive function, or in other embodiments, for treating cognitive dysfunction.

Accordingly, in one embodiment, the invention provides methods for treating a neurological condition comprising administering to a patient in need thereof a nutrient composition that ameliorates one or more symptoms of the neurological condition, said nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*, said neurological condition being selected from the group consisting of autism, apraxia, speech impairments, ADHD, traumatic brain injury, seizure disorders, epilepsy, and global delays, preferably autism or apraxia, more preferably autism. In certain alternatively preferred embodiments, the neurological condition is a seizure disorder. In other alternatively preferred embodiments, the neurological condition is a ADHD.

In certain other embodiments, the invention provides nutrient compositions comprising:

an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

In accordance with certain preferred aspects of the invention, there are provided methods of preventing inhibiting or treating apraxia, autism, speech impairments, traumatic brain injury, seizure disorders, epilepsy, global delays, or ADHD comprising the step of administering to said patient an effective amount of a nutrient composition of the invention including, for example, a composition comprising:

an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

Symptoms of one or more of the brain conditions where improvements may be observed include, for example, speech articulation, including complexity and sophistication of sentence structure; language skills such as improvements in the understanding of written and spoken word and/or development of better reading and writing skills; fine and gross motor skills including those related to multi-tasking abilities; imaginative play abilities; ocular and/or auditory focus including awareness of surroundings; sensory awareness (in situations where sensor integration dysfunction has been identified), non-verbal communication skills such as facial expressions; task focus; socialization skills; and reduced levels or substantial elimination of seizures or headaches, the reduced levels of which may result in a lowering or elimination of any seizure medication dosage levels deemed necessary. The improvement may also include normalization of EEG results.

While not desiring to be bound by any theory or theories of operation, it is believed that herbs like *emblica officinalis* (amalaki), *curcuma longa* (turmeric), *commiphora mukul*, (guggul) and/or *Gymnema* may work on opening the micro circulatory channels and may also regulate various endocrine pathways contributing to improved brain function. It is reasonably likely that there may be improved oxygenation to the brain and harmonious functioning of the right and left brain hemispheres because of reduced inflammation related to administration of such herbs.

In certain embodiments, the nutrient compositions are useful, inter alia, in methods for enhancing cognitive function. In other embodiments, the nutrient compositions are useful, inter alia, in methods for treating cognitive dysfunction.

In some embodiments, the invention relates to methods for enhancing cognitive function in patients by administering nutrient compositions that enhance one or more aspects of cognitive function—said nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*. In certain preferred embodiments, the nutrient composition further comprises an effective amount of an omega 3 fatty acid or pharmaceutically acceptable or food grade acceptable derivative thereof.

"Cognitive function", as used herein, refers to the function of the mental process of a human or other animal, who may be unhealthy or unhealthy, and includes at least three different components: attention, learning, and memory. See, e.g., *Mosby's Medical Dictionary*, 5$^{th}$ edition (1998); *Stedman's Medical Dictionary*, 11$^{th}$ edition (1990). In certain preferred embodiments of the invention, the method of the invention are useful for enhancing cognitive function, particularly memory, including enhancing the cognitive function, particularly memory, of a healthy or unhealthy patient. As used herein, "memory" refers to the complex mental function having at least four distinct phases: (1) memorizing or learning, (2) retention, (3) recall, and (4) recognition, and includes immediate, recent, and remote memory. See, e.g., *Mosby's Medical Dictionary*, 5$^{th}$ edition (1998); *Stedman's Medical Dictionary*, 11$^{th}$ edition (1990).

The term "enhancing", as used herein, refers to the ability of the compounds of the invention and/or composition containing them to increase the ability or capacity of an individual (healthy or unhealthy) to comprehend, judge, memorize, and reason; and can be measured by typically employed by those skilled in the art. Such an improvement can include at least about a 10% increase, preferably, at least about a 25% increase, and more preferably, at least about a 50% increase.

In other embodiments, the patient is suffering cognitive dysfunction. "Cognitive dysfunction", as used herein, refers to disturbances in the mental process related to thinking, reasoning, and judgment and includes, without limitation, memory loss. See, e.g., *Mosby's Medical Dictionary*, 5$^{th}$ edition (1998); *Stedman's Medical Dictionary*, 11$^{th}$ edition (1990). The term "cognitive dysfunction" indicates disruptions in performance including one or more of the following signs:

(1) memory deficits (impaired ability to learn new information or recall previously learned information;
(2) one (or more) of the following disturbances:
   (a) aphasia (language disturbance) [
   (b) apraxia (impaired ability to carry out motor activities despite intact motor function)
   (c) agnosia (failure to recognize or identify objects despite in tact sensory function); and/or
   (d) disturbance in executive functioning (i.e. planning, organizing, sequencing, abstracting);
(3) memory disturbances causing significant impairment in social or occupational functioning, and representing a significant decline from a previous level of functioning; and
(4) impairment in cognitive functioning as evidenced by neuropsychological testing or quantified clinical assessment, accompanied by objective evidence of a systemic general medical condition or central nervous system dysfunction.

Cognitive dysfunction is exhibited in certain diseases and disorders, including, but not limited to Alzheimer's Disease, mild cognitive impairment, age-related cognitive decline, vascular dementia, Parkinson's Disease dementia, amyotrophic lateral sclerosis, Huntington's Disease, stroke, traumatic brain injury, AIDS-associated dementia, schizophrenia, Lewy-body variant of Alzheimer's Disease with or without association with Parkinson's Disease, Creutzfeld-Jakob Disease, Korsakoff's Disorder, learning disabilities caused by degenerative disorders, learning disabilities caused by non-degenerative disorders, genetic conditions (e.g., Rubenstein-Taybi Syndrome), cerebral senility, vascular dementia, electric shock induced amnesia, memory impairment associated with depression or anxiety, memory impairment associated with surgical procedures such as coronary artery bypass grafting (CABG), Down's syndrome, and combinations thereof.

In certain embodiments of the methods of the invention, the cognitive dysfunction is memory loss, including memory loss that is age-associated, caused by electro-convulsive therapy, the result of brain damage, or a combination thereof. The brain damage may be caused by a stroke, an anesthetic accident, head trauma, hypoglycemia, carbon monoxide poisoning, lithium intoxication, vitamin deficiency (such as B1, thiamine and B 12), or a combination thereof.

Memory loss and impaired learning ability are features of a range of clinical conditions. For instance, loss of memory is the most common symptom of dementia states including Alzheimer's disease. Memory defects also occur with other kinds of dementia such as multi-infarct dementia (MID), a senile dementia caused by cerebrovascular deficiency, and the Lewy-body variant of Alzheimer's disease with or without association with Parkinson's disease, or Creutzfeld-Jakob disease. Loss of memory is a common feature of brain-damaged patients. Brain damage may occur, for example, after a classical stroke or as a result of an anesthetic accident, head trauma, hypoglycemia, carbon monoxide poisoning, lithium intoxication, vitamin (B1, thiamine and B12) deficiency, or excessive alcohol use or Korsakoff's disorder. Memory impairment may furthermore be age-associated; the ability to recall information such as names, places and words seems to decrease with increasing age. Transient memory loss may also occur in patients, suffering from a major depressive disorder, after electro-convulsive therapy (ECT).

Preferably, the nutrient compositions employed in the methods of the present invention are in granular or powder form; more preferably wherein the nutrient compositions are capable of being administered orally; still more preferably wherein the nutrient composition is combined with a liquid vehicle for oral consumption by the patient. In some preferred embodiments, the liquid vehicle comprises water or milk. In other preferred embodiments, the liquid vehicle comprises juice.

In certain preferred embodiments, the nutrient composition comprises a mixture or purified mixture thereof comprising botanical extracts selected from each of *gymnema sylvestre*, *commiphora mukul*, *curcuma longa*, *camellia sinensis*, *emblica officinalis*, and *terminalis chebula*. More preferably, the nutrient composition further comprises *cinnamomum verum* or *capsicum annuum*.

In other preferred embodiments the nutrient composition further comprises
  (a) whey protein isolate, L-taurine, L-theonine, vitamin A (e.g., as retinol palmitate), vitamin B-1 (e.g., as thiamine mononitrate), vitamin B-2 (e.g., as riboflavin), vitamin B-3 (e.g., as niacinamide), vitamin B-5 (e.g., as d-ca pantothenate), vitamin B-6 (e.g., as pyridoxine HCl), vitamin B-7 (e.g., as biotin), vitamin B-9 (e.g., as folic acid), vitamin B-12 (e.g., as cyanocobalamin), vitamin C (e.g., as ascorbic acid), vitamin D-3 (e.g., as cholecalciferol), and vitamin E (e.g., as d-alpha tocopherol), brown rice powder, sugar, apple fiber, cocoa powder, xanthan gum, potassium gluconate, calcium lactate, stevia, iodine yeast, chromium yeast, manganese yeast, zinc gluconate, selenium yeast, magnesium oxide, copper gluconate, and molybdenum yeast, and
  (b) cocoa flavor and *capsicum annuum*; or
  vanilla flavor and *cinnamomum verum*.

In some preferred embodiments, the nutrient composition further comprises one or more amino acids; more preferably wherein the amino acids are in the form of one or more whey protein isolates. In even more preferred embodiments, the one or more amino acids contained in the amino acid composition and/or contained in the one or more whey protein isolates are selected from the group consisting of: alanine, arginine, aspartic acid, cysteine, cystine, glutamic acid, glycine, histidine, isoleucine, leucine, lysine, methionine, phenylalanine, proline, serine, threonine, tryptphan, tyrosine, and valine. In certain alternatively preferred embodiments, the nutrient composition comprises each of the essential amino acids arginine, histidine, isoleucine, leucine, lysine, methionine, phenylalanine, threonine, tryptphanand valine.

While not desiring to be bound by any theory or theories of operation, it is believed that combinations of amino acids, preferably including one or more essential amino acids, such as those in the commercial product NutriiVeda™, for example, may assist and support the healing of neurotransmitter deficiency conditions such as seizures, depression, anxiety disorder, insomnia, Alzheimer's disease and/or Parkinson's disease.

In other preferred embodiments, the nutrient composition further comprises taurine or theonine; more preferably L-taurine or L-theonine.

In yet other preferred embodiments of the invention, the nutrient composition is gluten or casein free.

In certain preferred embodiments the nutrient composition further comprises at least one copper containing compound; more preferably wherein the nutrient composition comprises at least one copper containing compound and further comprises at least one additional metal containing compound, wherein the metal is selected from the group consisting of calcium, magnesium, zinc, selenium, manganese, chromium, and molybdenum. It may be advantageous in certain preferred embodiments to incorporate one or more of the metals selected from the group consisting of calcium, magnesium, zinc, selenium, manganese, chromium, and molybdenum as their yeast complexes. Accordingly, in certain more preferred embodiments, the selenium is provided as selenium yeast. In other more preferred embodiments, the manganese is provided as manganese yeast. In certain other more preferred embodiments, the chromium is provided as chromium yeast. In still other more preferred embodiments, the molybdenum is provided as molybdenum yeast.

In some preferred embodiments, the nutrient composition further comprises vitamins, preferably sourced from whey protein, botanicals or other natural sources including nutritional yeast or other natural food forms of vitamins.

In other preferred embodiments, the nutrient composition further comprises one or more vitamins; more preferably wherein the vitamin is selected from the group consisting of vitamin A, vitamin B-1 (thiamine), vitamin B-2 (riboflavin), vitamin B-3 (niacin), vitamin B-5 (pantothenic acid), vitamin B-6, vitamin B-7 (biotin), vitamin B-9 (folic acid), vitamin B-12, vitamin C, vitamin D-3, and vitamin E. In certain even more preferred embodiments, the one or more vitamins in an administered dose are present in the range of:
  from about 2000 IU to about 3000 IU of vitamin A;
  from about 1 mg to about 2 mg of vitamin B-1;
  from about 1 mg to about 2 mg of vitamin B-2;
  from about 10 mg to about 30 mg of vitamin B-3;
  from about 5 mg to about 15 mg of vitamin B-5;
  from about 1 mg to about 3 mg of vitamin B-6;
  from about 10 mcg to about 50 mcg of vitamin B-7;
  from about 200 mcg to about 600 mcg of vitamin B-9;
  from about 2 mcg to about 10 mcg of vitamin B-12;
  from about 30 mg to about 90 mg of vitamin C;
  from about 200 IU to about 600 IU of vitamin D-3; and
  from about 10 IU to about 50 IU of vitamin E.

In certain preferred embodiments the nutrient composition further comprises at least one protein source; more preferably wherein the at least one protein source comprises brown rice powder.

In some other preferred embodiments the nutrient composition further comprises at least one source of sugars, dietary fiber, or other carbohydrate.

In certain preferred embodiments, the nutrient composition contains other optional components, e.g., flavors or sweeteners to improve palatability, and/or preservatives to improve shelf life.

Preservatives may be added to the nutrient compositions according to the invention. Any suitable preservative can be employed, so long as the preservative does not negate other desirable properties of the nutrient supplements, or have undesirable side effects in persons (i.e., in autistic persons as compared with non-autistic persons). Preferred preservatives include, but are not limited to, sodium benzoate and potassium sorbate which can be obtained from any commercial supplier. Preferably these preservatives are of a high purity grade. For example, these preservatives can be obtained from Spectrum Quality Products, Inc. (Gardena, Calif., Catalog Numbers S1146 and P1408, respectively), or from Sigma-Aldrich (St. Louis, Mo., Catalog Numbers B3420 and 57420, respectively). Other appropriate preservatives are alcohol (from about 15 to about 20%), benzoic acid (about 0.1%), methylparaben (from about 0.025% to about 0.2%), propylparaben (from about 0.025% to about 0.2%), and sorbic acid (about 0.1%). Sodium benzoate and potassium sorbate (or other appropriate preservatives) also can be employed in the liquid formulations of the invention in amounts ranging from about 0.01% to about 1.0% by weight (mass/volume, such as g/l) of the liquid formulations, even more preferably from about 0.05% to about 0.5% by weight (mass/volume), and especially from about 0.1% by weight (mass/volume).

Optionally, sweeteners may be added to the nutrient compositions of the invention, for instance, to make the powder or liquid vehicle added formulations more palatable, e.g., sweeteners such as natural sugars (e.g., glucose, sucrose, fructose) and synthetic sugars (e.g., saccharin, cyclomates, Aspartame, etc.). In certain preferred embodiments, the nutrient compositions do not contain Aspartame or any of its chemically analogous equivalents. Care must be taken with use of natural fructose sweeteners, however, since a high fructose content has been suggested to exacerbate copper deficiency and to be associated with heart disease characterized by high triglyceride levels. Other preferred natural sweeteners that can be employed in the invention, include but are not limited to: Bee Honey (Dutch Gold Honey, Lancaster, Pa.); Organic Bee Honey (miscellaneous vendors); Barley Malt syrups (Briess Industries New York, N.Y.); deionized fruit juice (Daystar-Robinson, Lake Success, N.Y.); Fruitrim liquid (Adept Solutions); Brown rice syrups (California Natural Products Santa Barbara, Calif.); Organic brown rice syrup (California Natural Products); Oat syrup (T & A Gourmet); Raw or Turbinado sugar (C & H sugar La Palma, Calif.); Sucanat (Wholesome Foods Palm Bay, Fla.); Organic Sucanat (Wholesome Foods Palm Bay, Fla.); Organic Sugar (Wholesome Foods Palm Bay, Fla.); Evaporated cane juice (Florida Crystals Palm Beach, Fla.); and Ki-Sweet (kiwi fruit sweetener, marketed on the Internet), as well as other sweeteners. The amount of sweetener effective in the supplement depends on the particular sweetener used and the sweetness intensity desired, and can range from about 0.1% to about 70%.

In certain other preferred embodiments the nutrient composition further comprises iodine. In more preferred embodiments, the iodine is provided as iodine yeast complex.

In other preferred embodiments, the nutrient composition does not further comprise at least one of the following moieties: adenosine monophosphate, docosahexaenoic acid, and a sweetener containing 75% to 90% by weight of Lo Han Guo extract and 10 to 25% tagatose.

In certain alternatively preferred embodiments, the nutrient composition optionally further comprises less than 0.0002% by weight adenosine monophosphate based on the weight of the nutrient composition. Alternatively, the nutrient composition optionally further comprises more than 0.010% by weight adenosine monophosphate and less than 10% based on the weight of the nutrient composition, preferably 2%, more preferably less than 1%, with less than about 0.1% being even more preferred.

In certain preferred embodiments, the nutrient composition comprises nutrients derived from whole food sources or are in substantially the same form, more preferably the same form, as found in whole food sources.

It is believed the, compound names and abbreviations, as well as the plant extracts and biological names used herein correctly and accurately reflect the underlying compositions. However, the nature and value of the present invention does not depend upon the theoretical correctness of these names and abbreviations, in whole or in part. Thus it is understood that the compound names and abbreviations, as well as the plant extracts and biological names attributed to the correspondingly indicated compounds and extracts, are not intended to limit the invention in any way, including local origins of plant species, or restricting any compound, amino acid or component or mixture thereof to any specific tautomeric form(s) or to any specific optical or geometric isomer or mixture of isomers, except where such stereochemistry is clearly defined.

Although the nutrient compositions of the present invention may be administered as the pure ingredient mixtures, it is preferable to present the active ingredient mixture as a consumable composition. The invention thus further provides a consumable nutrient composition comprising, together with one or more carriers acceptable for consumption therefor. The carrier(s) must be acceptable in the sense of being compatible with the other ingredients of the composition and not deleterious to the recipient thereof. Non-limiting examples include brown rice powder, sugar, apple fiber, cocoa powder, and xanthan gum.

In addition to the food grade carrier, the extract(s) comprising the nutrient compositions of the present invention may be co-administered with at least one component comprising an omega 3 fatty acid, preferably EPA (Eicosapentaenoic acid) or DHA (Docosahexaenoic acid), or any combination thereof. The source of the fatty acid may be from animal fish, or plant origin and is typically derived from any of a number of fish oils including anchovy, sardine, or mackerel or their mixtures. Other fish with elevated levels of omega 3 fatty acids include salmon, tuna, cod liver and/or herring. Other potent sources of omega 3 fatty acids include algae, such as microalgae (such as *Crysthecodinium cohii* and *Schizochytrium*) and brown algae (kelp); and plankton. The omega 3 fatty acid may be provided in a native or readily isolated form, or in any of the myriad of purified forms that may be provided, or may take the form of a mixture of any one or more of the native, readily isolable or purified forms. In certain compositions the omega 3 fatty acid may be provided in its free acid form, or a derivative thereof, including but not limited to esters, especially purified esters; more preferably ethyl or mono-, di-, or tri-ester forms of glycerine; or other pharmaceutically or food grade acceptable derivatives known to the skilled artisan, including, for example pharmaceutically acceptable salts of EPA or DHA. Among the most common n-3 fatty acids found in nature are the following fatty acids: α-Linolenic acid (ALA), all-cis-7,10,13-hexadecatrienoic acid; Stearidonic acid (SDA), all-cis-6,9,12,15-octadecatetraenoic acid; Eicosatrienoic acid (ETE), all-cis-11,14,17-eicosatrienoic acid; Eicosatetraenoic acid (ETA), all-cis-8,11,14,17-eicosatetraenoic acid; (EPA), all-cis-5,8,11,14,17-eicosapentaenoic acid; Docosapentaenoic acid (DPA), all-cis-7,10,13,16,19-docosapentaenoic acid; Docosahexaenoic acid (DHA), all-cis-4,7,10,13,16,19-docosahexaenoic acid; Tetracosapentaenoic acid, all-cis-9,12,15,18,21-tetracosapentaenoic acid; and Tetracosahexaenoic acid (Nisinic acid), all-cis-6,9,12,15,18,21-tetracosahexaenoic acid.

It is further appreciated that while an omega 3 fatty acid or derivative thereof may be provided in purified form, it is often isolated in mixture with other fatty acids or their derivatives, including for example, omega 6 fatty acids. The ratio of omega 3 to omega 6 fatty is said to vary widely from source to source, for example, in canola oil (1:2); flaxseed oil (3:1); cold water fish oil (7:1) and in microalgae (22:6). Erasmus, Udo, *Fats and Oils.* 1986. Alive Books, Vancouver, p. 263. Preferably, in combination products of the present invention that include omega fatty acid components, preferably omega 6 fatty acid components, in addition to omega 3 fatty acids, the ratio of omega 3 to omega other additional omega fatty acid components, preferably omega 6, is from about 1 to 1 to about 100:1, more preferably from about 2 to 1 to about 50:1; still more preferably from about 3 to 1 to about 25 to about 1 and all combinations and subcombinations of ranges of ratios of omega 3 to omega 6 fatty acid components therein, wherein the ratios are expressed as a ratio of the weights of the omega unsaturated acid components.

In certain more preferred embodiments, the omega 6 fatty acid component comprises linolenic acid, still more preferably omega 6 gamma-linolenic acid (GLA), which may be provided in its free acid form, or a derivative thereof, including but not limited to esters, especially purified esters; more preferably ethyl or mono-, di-, or tri-ester forms of glycerine; or other pharmaceutically or food grade acceptable derivatives known to the skilled artisan, including, for example pharmaceutically acceptable salts of combination products of the present invention. Exemplary sources of GLA include for example borage seed oil (typically contains about 24% GLA) and primrose oil (typically contains about 8 to about 10% GLA). These oils may be used as isolated from their sources or further purified as recognized by those of ordinary skill in the art. Alternatively preferred in some embodiments as an omega 6 fatty acid is dihomo-ã-linolenic acid (DGLA), a 20-carbon ù-6 fatty acid with three cis double bonds; the first double bond is located at the sixth carbon from the omega end. DGLA is the elongation product of ã-linolenic acid (GLA; 18:3, ù-6). The eicosanoid metabolites of DGLA include Series-1 thromboxanes (thromboxanes with 1 double-bond), via the COX-1 and COX-2 pathways; Series-1 prostanoids, via the COX-1 and COX-2 pathways.[1]; and a 15-hydroxyl derivative that blocks the transformation of arachidonic acid to leukotrienes. See Fan, Yang-Yi and Robert S. Chapkin (9 Sep. 1998). "Importance of Dietary ã-Linolenic Acid in Human Health and Nutrition". Journal of Nutrition 128 (9): 1411-1414; and Belch, Jill J F and Alexander Hill. "Evening primrose oil and borage oil in rheumatologic conditions"; American Journal of Clinical Nutrition, Vol. 71, No. 1, 352S-356S, January 2000. All of these effects are reported to be anti-inflammatory, in marked contrast with the analogous metabolites of arachidonic acid (AA), which are the series-2 thromboxanes and prostanoids and the series-4 leukotrienes. In addition to yielding anti-inflammatory eicosanoids, DGLA competes with AA for COX and lipoxygenase, inhibiting the production of AA's eicosanoids.

Preferred compositions or preparations according to the present invention that include omega 3 fatty acid components may be prepared so that an oral dosage unit form contains from about 100 to about 5000 mg of an omega 3 fatty acid, more preferably from about 100 to about 3000, still more preferably from about 100 to about 1000 mg of omega 3 fatty acid or pharmaceutically acceptable or food grade acceptable derivative thereof.

Co-administration of the omega 3 fatty acid with a nutrient composition of the present invention may be provided by separate administration of a supplement comprising an omega 3 fatty acid at the same time or sequentially in any order at different points in time. Thus, each component may be administered separately but sufficiently closely in time so as to provide the desired therapeutic effect. Preferably, the omega 3 fatty acid is added to the nutrient composition for ease of administration. More preferably the nutrient composition is in powdered form. The omega 3 fatty acid in a fluid form is applied to or into the powdered nutrient composition; or it may be mixed with the nutrient composition as a powdered form of an omega 3 fatty acid or derivative thereof. In preferable embodiments wherein the omega 3 fatty acid or derivative thereof is in powdered form, said powdered form is an encapsulated form of the fatty acid, preferably microencapsulated form. A non-limiting example of a powdered form of omega 3 fatty acid is any one of a number of commercially available products, preferably microencapsulated omega 3 fatty acid compositions manufactured, sold, and/or distributed by Nordic Naturals, Inc., Watsonville, Calif. Any powder form of an omega 3 fatty acid composition for use in or with any of the products of the invention has a density preferably similar to, more preferably substantially the same as, the density of the powder form of the nutrient composition, at least in part to diminish or reduce settling of one of the powder components in the combination product. The preferential density of the omega 3 fatty acid (or derivative thereof) powder form may be inherent in the product or modified by any of a known number of methods known to the skilled artisan.

The omega 3 fatty acid combination products (products comprising nutrient compositions with added omega 3 fatty acid) of the present compositions may further include one or more other active ingredients that may be conventionally employed in nutrient composition products.

The nutrient compositions of the invention may be orally administered in an effective amount by any of the conventional techniques well-established in the medical field. The nutrient compositions of the invention may also be orally administered in an effective amount by combining the composition with one or more food or beverage products and administering the combination.

The compositions may be administered alone or may be combined with a consumable carrier selected on the basis of the chosen route of administration The relative proportions of active ingredient and carrier may be determined, for example, by the solubility and chemical nature of the ingredients in the nutrient composition, chosen route of administration and standard practice for food consumables.

Nutrient compositions as described herein may be orally administered to a mammalian host in a variety of forms adapted to the chosen route of administration.

The nutrient compositions may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active nutrient composition may be incorporated with excipient and used in the form of ingestible tablets, buccal tablets, troches, capsules, elixirs, suspensions, syrups, wafers, and the like. The amount of active nutrient composition in such therapeutically useful compositions is preferably such that a suitable dosage will be obtained. Preferred compositions or preparations according to the present invention may be prepared so that an oral dosage unit form contains from about 0.1 to about 5000 mg of three or more active botanical extracts selected from the group of botanicals consisting of *gymnema sylvestre, commiphora mukul, curcuma longa, camellia sinensis, emblica officinalis,* and *termi-*

*nalis chebula*, and all combinations and subcombinations of ranges and specific amounts of active botanical extract therein.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active peptide may be incorporated into sustained-release preparations and formulations.

The dosage of the nutrient composition of the invention may vary depending upon various factors such as, for example, the pharmacodynamic characteristics of the particular agent and its mode and route of administration, the age, health and weight of the recipient, the nature and extent of the symptoms, the kind of concurrent treatment, the frequency of treatment, and the effect desired. Generally, small dosages may be used initially and, if necessary, increased by small increments until the desired effect under the circumstances is reached.

Although the proper dosage of the nutrient compositions of this invention will be readily ascertainable by one skilled in the art, once armed with the present disclosure, typically a dosage of the nutrient composition of the invention, preferably a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*, still more preferably wherein the nutrient composition comprises each of the botanical extracts selected from the group of botanicals consisting of *gymnema sylvestre, commiphora mukul, curcuma longa, camellia sinensis, emblica officinalis*, and *terminalis chebula*. In certain preferred embodiments wherein NutriiVeda™ weight management shakes (as provided by Zrii®, LLC of Draper, Utah 84020) are used as the nutrient composition, the proper dosage may range from about 2 to 4 grams per day up to about 20 grams a day (may be split into half dosages twice a day) for patients in the age range of from birth to about three years. For those aged about four to about eight years, the dose may range from about 20 grams to about 40 grams a day (may be split into half dosages twice a day). For patients of from about nine years to adult, a typical dose is up to about 85 grams to about 125 grams a day, preferably split into 40-65 grams per serving. Preferably, initial administration of the composition is at about 20 grams increased to about 25 grams per day. In some instances, qualified medical personnel have employed higher dosages, such as with 3 year old children up to about 40 grams over time, with children between 4 and 8 up to about 65 grams over time.

The dose may also be provided by controlled release of the compound, by techniques well known to those in the art, such as microencapsulation. Microencapsulation is a preferred means of providing an omega 3 fatty acid or derivative thereof with or within compositions of the present invention, especially for those that may be administered in the treatment or inhibitions of apraxia, autism, speech impairments, traumatic brain injury, seizure disorders, epilepsy, global delays, or ADHD or any combination thereof.

The nutrient compositions may be mixed with any type of milk, juice, or water. However, it is preferable to mix the composition with the selected liquid vehicle at temperatures below about 100° C., more preferably below about 50° C., more preferably still at about room temperature and below to minimize any possible adverse affect on potency of the composition. The composition can also be mixed with ice cream or similar semi-frozen beverage.

A wide variety of food vehicles may be employed to assist in administration of the nutrient composition, such as yogurt, pudding, apple sauce, ketchup, ranch dressing or cake frosting. Some parents have sprinkled it over pancakes or cereal including oatmeal.

The nutrient compositions of the present invention preferably can contain other natural and man-made compounds such as would be appropriate for a particular application, e.g., other carriers, stabilizers, preservatives, active agents, etc., so long as these other compounds do not negate the desirable properties of the nutrient compositions. In particular, tablets optionally may contain suitable binders, lubricants, diluents, disintegrating agents, coloring agents, flow-inducing agents, melting agents, and the like. Liquid formulations optionally may contain suitable solvents, emulsifying agents, suspending agents, diluents, melting agents, coloring agents, and the like. Of course, any component that detracts from or negates the desirable benefits of other components present in the nutrient compositions, or which has negative effects in the persons being treated (e.g., autistic persons or persons predisposed to autism as compared with non-autistic persons or non-predisposed persons) should not be employed.

In certain preferred embodiments the nutrient composition for use in the methods of the present invention comprises any one of NutriiVeda™ weight management shake compositions provided by Zrii®, LLC of Draper, Utah.

Kits useful in, for example, for the treatment of apraxia, autism, TBI, global delays, ADHD, which comprise a therapeutically effective amount of a nutrient composition of the invention in one or more sterile containers are also within the ambit of the present invention. Kits useful in, for example, for the treatment of stroke, or seizures comprising a therapeutically effective amount of a nutrient composition of the invention in one or more sterile containers are also within the ambit of the present invention. Kits useful in, for example, for enhancing cognition, which comprise a therapeutically effective amount of a nutrient composition of the invention in one or more sterile containers are also within the ambit of the present invention. Sterilization of the container may be carried out using conventional sterilization methodology well known to those skilled in the art. The sterile containers of materials may comprise separate containers, or one or more multi-part containers. Instructions, either as inserts or as labels, indicating quantities of the components to be administered, guidelines for administration, and/or guidelines for mixing the components, may also be included in the kit.

It will be further appreciated that the amount of the nutrient composition required for use in treatment will vary not only with the particular composition selected but also with the nature of the condition being treated and the age and condition of the patient, and will be ultimately at the discretion of the attendant administering the composition.

The desired dose may conveniently be presented in a single dose or as divided doses administered at appropriate intervals, for example, as two, three, four or more sub-doses per day.

In certain preferred aspects, the methods comprise the step of administering to said patient an effective amount of a nutrient composition.

The nutrient compositions of the present invention may be utilized in a number of ways. In certain embodiments, the nutrient compositions are useful, inter alia, in methods for treating apraxia, autism, traumatic brain injury, global delays, or ADHD, or any of the related symptoms of apraxia, autism, traumatic brain injury, global delays, or ADHD.

Thus, in accordance with preferred aspects of the invention, there are provided methods of preventing or treating apraxia, autism, speech impairments, traumatic brain injury, seizure disorders, epilepsy, global delays, or ADHD, or any of the related symptoms of apraxia, autism, speech impairments, traumatic brain injury, seizure disorders, epilepsy, global delays, or ADHD.

In certain embodiments, the nutrient compositions are useful, inter alia, in methods for treating stroke.

Thus, in accordance with preferred aspects of the invention, there are provided methods of preventing or treating stroke, or any of the related symptoms of stroke.

When any variable occurs more than one time in any constituent or in any composition, its definition in each occurrence is independent of its definition at every other occurrence.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

The present invention will now be illustrated by reference to the following specific, non-limiting examples. Those skilled in the art of organic synthesis may be aware of still other synthetic routes to the invention peptides. The reagents and intermediates used herein are commercially available or may be prepared according to standard literature procedures. These examples are for illustrative purposes only, and are not to be construed as limiting the appended claims.

EXPERIMENTAL SECTION

The following procedures may be employed as a manner of measuring qualitative and/or quantitative effects that result from administration of various nutrient compositions of the present invention to a patient in need thereof, including effects such as behavioral modifications, cognition enhancement and/or anti-convulsant activity
Evaluation of Principal Effects of Compositions of the Present Invention Principal effects of a composition of the present invention may be evaluated using the Primary Observation (Irwin) Test in the mouse. See Irwin (*Psychopharmacologia,* 13, 222-257, 1968). This method detects the first toxic dose, the active dose-range and the principal effects of a test substance on behavior and physiological function. Mice are administered the test substance and are observed in simultaneous comparison with a control group given vehicle (non-blind conditions). Between 1 and 3 treated groups are compared with the same control at any one time. All animals within a treatment group are observed simultaneously.

Behavioral modifications, physiological and neurotoxicity symptoms, rectal temperature and pupil diameter are recorded according to a standardized observation grid derived from that of Irwin. The grid contains the following items: death*, convulsions*, tremor*, Straub tail*, altered activity, jumping*, abnormal gait* (rolling, tiptoe), motor incoordination*, altered abdominal muscle tone, loss of grasping, akinesia, catalepsy, loss of traction, writhing*, piloerection*, stereotypies* (sniffing, chewing, head movements), head-twitches*, scratching*, altered respiration*, aggression*, altered fear/startle, altered reactivity to touch, ptosis, exophthalmia, loss of righting reflex, loss of corneal reflex, analgesia, defecation/diarrhea, salivation, lacrimation, rectal temperature (hypothermia/hyperthermia) and pupil diameter (myosis/mydriasis).

Observations are performed 15, 30, 60, 120 and 180 minutes after administration of the test substance and also 24 hours later. The symptoms marked (*) are observed continuously from 0 to 15 minutes after administration.

Raw data are entered into calculation spreadsheets. All data entered are compared with raw data by two persons to verify entry accuracy before data analysis.

In grouped data tables: qualitative data are presented as presence/absence, or decrease/increase, of the behavioural symptoms. Rectal temperature and pupil diameter are measured quantitatively and are presented as means followed by ± sign and the standard error of the mean (s.e.m.) and as variation (delta) from control at each time point.

In summary tables: qualitative data are presented as the number of animals showing the symptoms (with their intensity (slight, moderate or marked) for decrease or increase in movements). Rectal temperature and pupil diameter are graded on a 3-point scale (slight, moderate or marked) in terms of the direction change from control values.
Evaluation of Cognition Enhancing Activity Using the Social Recognition Test in the Rat (Delay Induced Deficit).

Memory or cognition enhancing activity may be measured following the procedure described by Lemaire et al. (Psychopharmacology, 115, 435-440, 1994). As one way of estimating cogntition enhancement, compositions of the present invention are tested as follows:

An unfamiliar juvenile is introduced into the individual home cage of a mature adult rat for 5 minutes. Following this first contact (C1), the juvenile is returned to its isolation cage for 120 minutes and reintroduced for a second contact of 5 minutes with the same mature adult rat (C2).

The time the adult rat spends investigating (sniffing, grooming, licking, closely following) the juvenile at each contact is recorded. A recognition index (=C2/C1) is also calculated. Under such conditions, a mature adult rat failure to recognize the juvenile as familiar is indicated by an absence of reduction in the duration of social investigatory behavior at C2.

The test substances are evaluated at 2 doses, administered p.o. immediately after before C1 (i.e. 120 minutes before C2), and compared with a vehicle control group. The test is performed blind. Donepezil HCl (3 mg/kg i.p.) administered immediately after C1 is used as reference substance.

Data are analyzed by comparing treated groups with control using one-way Anova followed by post-hoc analysis.

Raw data are entered into calculation spreadsheets previously verified and protected using a standard commercial spreadsheet product. All data entered are compared with raw data by two to verify entry accuracy before data analysis. Results in grouped data tables or figures are presented as means followed by a ± sign and the standard error of the mean (s.e.m.) (parametric data) or as medians followed by [interquartile ranges] (non-parametric data). All differences are considered statistically significant when the null hypothesis can be rejected at a risk a of less than 0.05.

Evaluation of Anticonvulsant Activity for Compositions of the Present Invention Using the 6 Hz Psychomotor Test in the Mouse.

Anticonvulsant activity may be measured by the following method as described by Brown et al. (*J. Pharmacol. Exp. Ther.* 107, 273-283, 1953), which detects anticonvulsant activity.

Mice are administered a rectangular current (44 mA, rectangular pulse: 0.2 ms pulse width, 3 s duration, 6 Hz) via corneal electrodes connected to a constant current shock generator (Ugo Basile: Type 7801). The results for the number of seizures as reflected by forelimb clonus and Straub-tail are recorded during the first minute following current administration. Forelimb clonus is scored as absent (0), mild (1) and strong (2) whereas Straub tail is rated as absent (0) or present (1). 15 mice are studied per group. The test is performed blind.

Each composition is evaluated at 2 doses, administered p.o. 60 minutes before the test and compared with a vehicle control group. Diazepam (8 mg/kg p.o.), administered under the same experimental conditions, is used as reference substance.

Quantitative data (scores) with the tested compositions are analyzed by comparing treated groups with vehicle control using the Kruskal-Wallis test followed by the Mann-Whitney U test. Quantitative data with the reference substance are analyzed using the Mann-Whitney U test.

Quantal data (Straub tail) will be analyzed by comparing treated groups with the vehicle control using Fisher's Exact Probability tests.

The examples that follow are directed to in vivo experiments in humans which demonstrate the effectiveness of the methods of the present invention. They represent anecdotal reports gathered from parents and/or attending physicians regarding improvements in patients attributed to administration of NutriiVeda™, a nutrient composition that is administered in certain preferred embodiments of the present invention.

Example 1

A nine year old male patient was administered 2 scoops (approximately 40 grams) of NutriiVeda™ on a once per day basis. Prior to administration, the patient had been having uncontrolled seizures for three years in spite of continuing administration of seizure medications. Soon after administration was begun, slight improvements in mood, temper, and language comprehension were observed. Dosage was increased to approximately 40 grams twice per day basis. The patient was seizure-free for 15 weeks and the dosage level of his seizure medication was reduced on two occasions.

Example 2

A 4½ year old male patient was diagnosed with high functioning autism and severe oral and verbal apraxia (also a milder limb apraxia). The patient was administered 2 scoops (approximately 40 grams) of NutriiVeda™ on a once per day basis. After two weeks, the improvements in written language recognition and related speech were observed. The patient began spelling out words after week 3 and counting up to 10.

Example 3

A thirteen year old male patient diagnosed with apraxia showed improvements in speech after administration of 2 scoops (approximately 40 grams) of NutriiVeda™) on a twice per day basis. After one week the patient's language was observed to be smoother and faster. At a later time, administration of NutriiVeda™ was reduced to 2 scoops (approximately 40 grams) of NutriiVeda™) at breakfast on one day and 2 scoops (approximately 40 grams) of NutriiVeda™) the next night. The parent noticed that the patient's speech had regressed at the end of this period of reduced administration. Administration was increased to earlier levels and subsequently increased to 3 scoops (approximately 60 grams) of NutriiVeda™) on a twice per day basis. In the weeks that followed the patient's speech improved. Additionally the patient began waking up each morning prior to his alarm, showed greater interest in reading and sharing the books he was reading (in detail), read a chapter book in two days, had a sudden ability to independently blink one eye at a time. The male patient's chief school administrator confirmed that was more alert, participated more in class and showed improved speech abilities.

Example 4

A male child patient diagnosed with apraxia at three years of age was initially administered 1 scoop (approximately 20 grams) of NutriiVeda™ on a once per day basis with a gradual increase to two scoops (approximately 40 grams) per day over a one month period. The attending speech language pathologist subsequently indicated that the patient showed fewer signs of classic apraxia and noted that the patient's apraxia symptoms have been reduced such that they now more resemble a phonological processing. After one month of taking NutriiVeda™, the patient's word usage, conversation skills, language comprehension and fine motors skill levels improved.

Example 5

A speech language pathologist from Marriottsville, Md. reported the following observations regarding a client diagnosed with apraxia.

A six year old male patient diagnosed with global apraxia w/fine motor and sensory challenges was administered 1 scoop (approximately 20 grams) of NutriiVeda™ in a chocolate pudding delivery vehicle on a once per day basis. Subtle changes in fine motor skills were observed such as writing his name by connecting the dots; greater willingness to try school work and practice (many more attempts to imitate words in isolation and in combination); multitasking-today during play; and displaying a sense of humor while using his words Example 6

A 34 month old male patient was diagnosed with Childhood Apraxia of Speech at 24 months. He was administered 1 scoop (approximately 20 grams) of NutriiVeda™) on a once per day basis. After five days the patient's mood and demeanor improved and resistance to parental instruction decreased. The patient demonstrated improved peace/calmness. His verbal language skills showed more complex language use, and the patient's articulation of consonants was much clearer and completion of word end sounds was enhanced relative to his efforts prior to administration. His abilities to focus for extended periods were enhanced. His therapist has noted that the patient is making sounds easier and that his focus was significantly better.

Example 7

A 5 year old male patient was diagnosed with Childhood Apraxia of Speech. He was administered 1.5 scoops (approximately 30 grams) of NutriiVeda™) on a twice per day basis. The patient drank a glass of water prior to administration of the NutriiVeda™. Initially the NutriiVeda™ was mixed with DariFree chocolate. Subsequently, the DariFree chocolate was substituted by water. Within six weeks, the patient required much less translation from a parent to communicate with others. In addition, the patient increased his standard score from 69 to 89 on the Goldman Fristoe Test of Articulation. The patient also showed improvement in behavior, song singing, and motor skills. Upon re-evaluation by a neurologist, his diagnosis was downgraded from severe apraxia to mild to moderate apraxia, extending to limbs.

Example 8

A nine year old male patient diagnosed with severe apraxia, mild PDD/NOS, and seizure disorder was scheduled for a partial lobotomy. The patient was administered 2 scoops (approximately 40 grams) of NutriiVeda™ on a twice per day basis. Prior to administration, the patient had been having uncontrolled seizures with a periodicity of less than or equal to 2 weeks. Within 2 to 3 weeks of the initial of NutriiVeda™ administration, slight improvements in articulation, overall intelligibility, more sophisticated use of language, awareness of surroundings, and spontaneity of speech were observed. The patient has been seizure-free for 9 months at this dosage level. In view of the lack of seizures, the surgery was postponed indefinitely and the patient was taken off the seizure control medications Depakote and Corbotrol.

Subsequently, the parent reduced dosage of the nutrient composition in half for several months. The child's SLP noticed a reduction in earlier speech/language gains. The parent then discontinued NutriiVeda™ for about two weeks to give her son a "break" from administration. Shortly (about 3 days) after reinitiating administration of the composition, the patient had his first seizure in over a year.

Example 9

A six and one half year old male patient predisposed to seizures and diagnosed with severe apraxia, autism/PDD and hypotonia, seizure disorder was administered 2 scoops (approximately 40 grams) of NutriiVeda™ on a twice per day basis for one week. The dosage was increased to 3 scoops (approximately 60 grams) of NutriiVeda™ on a once per day basis thereafter. After administration was begun, improvements in speech skills, social skills, awareness of surroundings, gross and fine motor skills and mood were observed. There was a decrease in the frequency/and/or severity of seizures leading to a decrease in administration levels of Topomax (for seizures) and Clonadine (for sleep assistance).

Example 10

A 10 year old female patient diagnosed with severe apraxia/dyspraxia and severe autism/PDD and predisposed to seizures was administered 2 to 4 scoops (approximately 40 to 80 grams) of NutriiVeda™ split up during the day. The dosage was provided as a shake with milk, or frozen into a popsicle or ice cream. Prior to administration, the patient had been having uncontrolled seizures even while sleeping despite continuing administration of seizure medication. After four weeks of NutriiVeda™ administration, improvements in articulation, intelligibility, oral motor skills, vocabulary gross and fine motor skills, focus, and mood were observed. The intensity and frequency of seizures has subsided.

Example 11

A 2 year old female patient diagnosed with apraxia and hypotonia was administered 1 scoop (approximately 20 grams) of NutriiVeda™ split up during the day. The dosage was provided as a shake with milk. After 4 weeks, improvements in sound production, articulation, overall intelligibility, motor planning, vocabulary, gross and fine motor skills, multi tasking, focus and mood were observed.

Example 12

A 3 year old male patient diagnosed with severe apraxia and gross and fine motor skill delays was administered 1 scoop (approximately 20 grams) of NutriiVeda™ split up during the day for two weeks. The dosage was provided as a shake with milk. After 2 weeks, improvements in sound production, articulation, overall intelligibility, social skills, learning skills, multi tasking, focus and mood were observed.

Example 13

A 4 year old male patient diagnosed with moderate autism/PDD was administered 1 scoop (approximately 20 grams) of NutriiVeda™ on a once per day basis. The dosage was provided as a shake with milk. Slight improvements were noted within 3 to 5 days. After 6 weeks, improvements in sound production, oral motor dysfunction, receptive language skills, expressive language skills, social skills, gross and fine motor skills, multi tasking, focus and mood were observed.

Example 14

A 3 year old male patient diagnosed with severe apraxia and dysarthria (weakness of facial muscles) was administered 1 scoop (approximately 20 grams) of NutriiVeda™ on a once per day basis. The dosage was provided as a shake with milk. After 2 weeks, improvements in sound production, articulation, overall intelligibility, oral motor dysfunction, receptive language skills, expressive language skills, social skills, fine motor skills, learning skills, multi tasking, focus and mood were observed.

Example 15

A 10 year old male patient diagnosed with severe apraxia, motor planning an sensory dysfunction was administered 2 scoops (approximately 40 grams) of NutriiVeda™ on a twice per day basis for five weeks. The dosage was provided as a shake with milk or juice, or mixed in a pudding, yogurt, applesauce, or peanut butter food vehicle. Slight improvements were noted within 3 to 5 days. After 5 weeks, improvements in sound production, articulation, overall intelligibility, motor planning, receptive language skills, expressive language skills, social skills, learning skills, fine motor skills, multi tasking, focus and mood were observed.

Example 16

A 3 year old male patient diagnosed with mild apraxia, feeding and swallowing disorders, and sensory integration dysfunction was administered 1 scoop (approximately 20 grams) of NutriiVeda™ split up over the day for four weeks. The dosage was provided as a shake with juice. Slight improvements were noted within 3 to 5 days. After 5 weeks, improvements in sound production, articulation, overall intelligibility, expressive language skills, social skills, fine motor skills, focus and mood were observed.

Example 17

An eighty nine year old male patient was diagnosed with Alzheimer's 9 years previously. His condition had progressed to a point where he was unaware of his surroundings, unable to care for himself, unable to walk without falling, and unable to speak. He was being considered as a nursing home resident based on his needed care requirements. His caregiver began administering 1 scoop (approximately 20 grams) of NutriiVeda™ four times a day (total of 4 scoops) and at times up to six times a day thereafter. Improvements in speech skills were noted within one day after the onset of NutriiVeda™ administration. Within a month the patient showed observable improvements in lucid conversation, awareness of surroundings, personal care, and ability to walk without falling as noted by the family and the patient's doctor. The recommendation for nursing home admittance was withdrawn.

Example 18

A thirty five year old male was diagnosed with severe stroke in the left hemisphere right in the speech center of the brain from a severed carotid artery. While under induced coma, part of his skull was removed for brain swelling. Shortly after returning home to continue his recovery, his mother began to administer one scoop/day of NutriiVeda™. His mother observed a reduction followed by an absence of the patient's severe headaches. The mother subsequently increased her son's dosage to four scoops a day. At the time that the increased dosage was initiated, the patient's speech was 23% intelligible. It was his doctor's prognosis at that time that the patient would never again be able to speak clearly based on the location in the brain where the stroke occurred and its effect on that brain region. To the contrary, the patient had rapid improvements including in his speech. In four months, his speech intelligibility rose to 82%. He had other noted improvements in movements to his right arm and leg relative to his earlier paralytic state.

Example 19

A six and a half year old male was diagnosed with severe autism, mental retardation, medication resistant epilepsy (Grand Mal seizures) and hypotonia. He had been under the care of the same neurologist all his life and was on three medications, two for seizures and one for sleep. Prior to the time he was administered NutriiVeda™, he made essentially no gains in any area in is IEP goals and was in a wheelchair, unable to perform even simple skills. He was put on somewhat less than 4 scoops of NutriiVeda™ daily for over a year. Within the first month, he started to play, smile, and climb, and became curious about his surroundings. He began to act like a normal child. Within the first six months of being on his daily regimen of NutriiVeda™ he was taken off all three of his medications and remains seizure free with no sleep issues. He met all his goals on his IEP and new aggressive goals were set for him. His long-time neurologist from Kaiser Permanente Santa Clara Medical Center stated he has two other patients with similar characteristics that were administered NutriiVeda™ with similar results.

Example 20

Five year old female was diagnosed with severe autism, hypotonia, global delays, and chronic constipation. Numerous therapies and strategies as well as special diets had been tried with little or no positive results. She was administered a regimen of two scoops of NutriiVeda™ per day. Within one week she began playing with a doll and other toys that had all been previously ignored. She also took an interest in an iPad™ and started playing some age and/or skill appropriate computer games on her own. She subsequently developed motor skills sufficient to carry her toys and iPad up to and into a chair to play which was previous impossible for her without assistance. She also began to walk around the house unassisted. She became openly affectionate for the first time. She was also able to move her bowels for the first time on her own.

Example 21

A fifteen year old male with autism and mental retardation was put on a regimen of four scoops a day of NutriiVeda™. Prior to beginning this regimen, his IQ was 47. Within 3 months he began to perform skills that he was unable to perform previously, such as removing a carton of milk from the refrigerator on his own and pouring himself a glass of milk. After 3 months on his regimen of NutriiVeda™, his IQ improved to 62.

Example 22

A sixteen year old male was diagnosed with ADHD. His high school reported that his focus was poor and he was floundering in his grades. He was put onto four scoops of NutriiVeda™ per day. Almost immediate improvements were noted in his focus. There were also improvements noted in his maturity, social skills and communication. His parents received certificates from three of his teachers in recognition of improvement in his abilities at school. He maintained these improvements on a regular regimen of from two to four scoops per day and is currently a straight A student.

Example 23

A thirty seven year old woman, mother of four, was diagnosed four years ago with partial absence seizures due to a lesion in her right front temporal lobe caused by radiation treatment for cancer. She was never seizure free for more than three days. She self-administered NutriiVeda™ on a one scoop per day regimen for one month. During this time she went for 12 days without a seizure. When she ran out of Nutriiveda she decided to stop her regimen and her seizures began again. Once she reinitiated her administration of NutriiVeda™, her seizures stopped. Subsequently, she administered NutriiVeda™ each day for 4 months on a one scoop per day regimen. She then voluntarily stopped taking NutriiVeda™ and has remained free of seizures (one month so far).

Example 24

A four and a half year old girl was diagnosed with global delays, was still unable to walk, and had medication-resistant Grand Mal seizures. She was put on a NutriiVeda™ administration schedule of two scoops a day. Within one week she was able to walk across a room and has stopped having seizures. After six months on her regimen, she is both walking and talking and has remained seizure free.

Example 25

A male aged 4 years and nine months was diagnosed as mosaic with a partial duplication on Chromosome 19 has been on both fish oils and NutriiVeda™ for about one year. One year ago, he started a regimen of ProEFA fish oils (one capsule a day). Within three weeks he went from saying "cu" to "cup". Within a few months started putting a few simple two word sentences together such as "go bye" however most of his speech was still limited to single word utterances. Subsequently he started a regimen of NutriiVeda™ in combination with the fish oil capsules. Within days his speech improved both in clarity and in length of sentences which was observed by professionals that worked with him. The professionals indicated that it was like a "fog was clearing" in the patient's brain. Within one month of starting NutriiVeda™ at one scoop a day together with his one capsule of ProEFA fish oil he started riding his tricycle for the first time. Six months later his mother increased his dosage of NutriiVeda™ to two scoops and again within days his speech increased to eight word sentences such as "I want a cup of apple juice, mama" While over the next four months the most dramatic improvements was in speech, he continued progress in fine and gross motor skills as well. One area that had not improved was his stimming; jumping and rubbing his fingers together when he was excited. His dosage of NutriiVeda™ was raised to three scoops per day. Shortly thereafter, he developed an ability to control his stimming for the first time.

Example 26

A male aged 3 years and 10 months who was diagnosed with apraxia was put on one scoop of NutriiVeda™ per day regimen. Previous to taking NutriiVeda™, he was essentially nonverbal, non compliant in therapy, lacking in social skills, with no interest in any books, spelling or counting. During the first week of being on NutriiVeda™ he started to talk and develop more appropriate social skills. Within the first month he started speaking in understandable 3 and 4 word sentences and developed an interest in books, spelling, and writing his name. After a month, the regimen was revised to include one capsule a day of ProEFA fish oils (manufactured by Nordic Naturals). Within a week he increased up to 9 word sentences. For example to his grandmother whom he calls "Momo", the male patient said "Momo, I luv you to moon to you home". After starting back to school and being without speech therapy for three months (summer holiday), he started back to preschool and both the teacher as well as the principal were elated over his progress. While it is typical that children with apraxia regress without instruction over the summer months, the speech therapist noted significant improvement in this case and documented that the patient's speech was easier to understand and that he was answering questions in the classroom.

Example 27

Improvement in Cognitive Function and Academics
Case

A seventeen year old female senior high school student was put on a regimen of 4 scoops of NutriiVeda™ split up during the day. Prior to the start of this regimen, her grades were primarily Bs and Cs. In social settings among peers, she showed symptoms of anxiety and insecurity. Almost immediately, her mother reported that her daughter seemed more motivated to do her school work. As the weeks progressed, she expressed interest in improving her grade point average. By the end of that school semester (about 3 months later), she was a straight A student. She became easy going and sociable with her peers, joining after school activities such as theater. After high school graduation, she was accepted into the Academy of Art University in San Fransisco where she majored in theater. She has continued to do well academically on her NutriiVeda™ regimen of 4 scoops per day.

Example 28

Improvement in Cognitive Function and Academics
Case

A fourteen year old male was put on a regimen of 4 scoops of Nutriiveda split up during the day. Prior to the start of this regimen, his grades were Bs and Cs. His parents' main concern was lack of popularity among other students in the school. He was teased and insecure. Within weeks of being on NutriiVeda™ he appeared to be more confident. He became more outgoing at school and started joining after school activities and making new friends. His mother described it as "suddenly came out of his shell". That semester his grades went from Bs and Cs to solid As and within a year of being on NutriiVeda™ he was asked to join the National Honors Society. This past summer, he saved up his own money to pay for a summer math class that enabled him to take more AP classes in high school this year. He ran for class president this year at school and won.

[Embodiment 1] A method for treating apraxia, autism, speech impairments, traumatic brain injury, seizure disorders, epilepsy, global delays, or ADHD, comprising administering to a patient in need thereof a nutrient composition that ameliorates one or more symptoms of apraxia, autism, speech impairments, traumatic brain injury, seizure disorders, epilepsy, global delays, or ADHD, said composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

[Embodiment 2] A method according to Embodiment 1, for treating apraxia or autism, or one or more symptoms thereof.

[Embodiment 3] A method according to Embodiment 1 or 2, for treating apraxia or one or more symptoms thereof.

[Embodiment 4] A method according to Embodiment 1 or 2, for treating autism, or one or more symptoms thereof.

[Embodiment 5] A method according to any one of Embodiments 1, 2, 3, and 4, wherein the nutrient composition is in granular or powder form.

[Embodiment 6] A method according to any one of Embodiments 1, 2, 3, 4, and 5, wherein the nutrient composition is capable of being administered orally.

[Embodiment 7] A method according to any one of Embodiments 1, 2, 3, 4, 5 and 6, wherein the nutrient composition is combined with a liquid vehicle for oral consumption by the patient.

[Embodiment 8] A method according to Embodiment 7, wherein the liquid vehicle comprises water or milk.

[Embodiment 9] A method according to any one of Embodiments 1, 2, 3, 4, 5, 6, 7, and 8, wherein the nutrient composition comprises a mixture or purified mixture thereof comprising botanical extracts selected from each of *gymnema sylvestre, commiphora mukul, curcuma longa, camellia sinensis, emblica officinalis*, and *terminalis chebula*,

[Embodiment 10] A method according to any one of Embodiments 1, 2, 3, 4, 5, 6, 7, 8, and 9, wherein the nutrient composition further comprises *cinnamomum verum* or *capsicum annuum*.

[Embodiment 11] A method according to any one of Embodiments 1, 2, 3, 4, 5, 6, 7, 8, 9, and 10, wherein the nutrient composition further comprises an amino acid composition comprising one or more amino acids.

[Embodiment 12] A method according to Embodiment 11, wherein the amino acid composition comprises a whey protein isolate.

[Embodiment 13] A method according to Embodiment 11 or 12, wherein the one or more amino acids contained in the amino acid composition are selected from the group consisting of: alanine, arginine, aspartic acid, cysteine, cystine, glutamic acid, glycine, histidine, isoleucine, leucine, lysine, methionine, phenylalanine, proline, serine, threonine, tryptphan, tyrosine, and valine.

[Embodiment 14] A method according to any one of Embodiments 1, 2, 3, 4, 5, 6, 7, 8, 9, 10, 11, 12, and 13, wherein the nutrient composition is gluten or casein free.

[Embodiment 15] A method according to any one of Embodiments 1, 2, 3, 4, 5, 6, 7, 8, 9, 10, 11, 12, 13, and 14, wherein the nutrient composition further comprises taurine or theonine.

[Embodiment 16] A method according to Embodiment 15, wherein the taurine is L-taurine and the theonine is L-theonine.

[Embodiment 17] A method according to any one of Embodiments 1, 2, 3, 4, 5, 6, 7, 8, 9, 10, 11, 12, 13, 14, 15, and 16, wherein the nutrient composition further comprises at least one copper containing compound.

[Embodiment 18] A method according to Embodiment 17, wherein the copper compound containing nutrient composition further comprises at least one metal containing compound, wherein the metal is selected from the group consisting of calcium, magnesium, zinc, selenium, manganese, chromium, and molybdenum.

[Embodiment 19] A method according to any one of Embodiments 1, 2, 3, 4, 5, 6, 7, 8, 9, 10, 11, 12, 13, 14, 15, 16, 17, and 18, wherein the nutrient composition further comprises at least one vitamin.

[Embodiment 20] A method according to any one of Embodiments 1, 2, 3, 4, 5, 6, 7, 8, 9, 10, 11, 12, 13, 14, 15, 16, 17, 18, and 19, wherein the at least one vitamin is selected from the group consisting of vitamin A, vitamin B-1 (thiamine), vitamin B-2 (riboflavin), vitamin B-3 (niacin), vitamin B-5 (pantothenic acid), vitamin B-6, vitamin B-7 (biotin), vitamin B-9 (folic acid), vitamin B-12, vitamin C, vitamin D-3, and vitamin E.

[Embodiment 21] A method according to any one of Embodiments 1, 2, 3, 4, 5, 6, 7, 8, 9, 10, 11, 12, 13, 14, 15, 16, 17, 18, 19, and 20, wherein the nutrient composition further comprises at least one protein source.

[Embodiment 22] A method according to 21, wherein the at least one protein source comprises brown rice powder.

[Embodiment 23] A method according to any one of Embodiments 1, 2, 3, 4, 5, 6, 7, 8, 9, 10, 11, 12, 13, 14, 15, 16, 17, 18, 19, 20, 21, and 22, wherein the nutrient composition further comprises at least one source of sugars, dietary fiber, or other carbohydrate.

[Embodiment 24] A method according to Embodiment 20, wherein the one or more vitamins in an administered dose are present in the range of:
from about 2000 IU to about 3000 IU of vitamin A;
from about 1 mg to about 2 mg of vitamin B-1;
from about 1 mg to about 2 mg of vitamin B-2;
from about 10 mg to about 30 mg of vitamin B-3;
from about 5 mg to about 15 mg of vitamin B-5;
from about 1 mg to about 3 mg of vitamin B-6;
from about 10 mcg to about 50 mcg of vitamin B-7;
from about 200 mcg to about 600 mcg of vitamin B-9;
from about 2 mcg to about 10 mcg of vitamin B-12;
from about 30 mg to about 90 mg of vitamin C;
from about 200 IU to about 600 IU of vitamin D-3; and
from about 10 IU to about 50 IU of vitamin E.

[Embodiment 25] A method according to any one of Embodiments 1, 2, 3, 4, 5, 6, 7, 8, 9, 10, 11, 12, 13, 14, 15, 16, 17, 18, 19, 20, 21, 22, 23, and 24, wherein the nutrient composition further comprises iodine.

[Embodiment 26] A method according to any one of Embodiments 1, 2, 3, 4, 5, 6, 7, 8, 9, 10, 11, 12, 13, 14, 15, 16, 17, 18, 19, 20, 21, 22, 23, 24, and 25, wherein the nutrient composition further comprises (a) whey protein isolate, L-taurine, L-theonine, vitamin A (as retinol palmitate), vitamin B-1 (as thiamine mononitrate), vitamin B-2 (as riboflavin), vitamin B-3 (as niacinamide), vitamin B-5 (as d-ca pantothenate), vitamin B-6 (as pyridoxine HCl), vitamin B-7 (as biotin), vitamin B-9 (as folic acid), vitamin B-12 (as cyanocobalamin), vitamin C (as ascorbic acid), vitamin D-3 (as cholecalciferol), and vitamin E (as d-alpha tocopherol), brown rice powder, sugar, apple fiber, cocoa powder, xanthan gum, potassium gluconate, calcium lactate, stevia, iodine yeast, chromium yeast, manganese yeast, zinc gluconate, selenium yeast, magnesium oxide, copper gluconate, and molybdenum yeast, and (b) cocoa flavor and *capsicum annuum*; or
vanilla flavor and *cinnamomum verum*.

[Embodiment 27] A method according to any one of Embodiments 1, 2, 3, 4, 5, 6, 7, 8, 9, 10, 11, 12, 13, 14, 15, 16, 17, 18, 19, 20, 21, 22, 23, 24, 25, and 26, further comprising an effective amount of an omega 3 fatty acid or pharmaceutically acceptable or food grade acceptable derivative thereof.

[Embodiment 28] A method according to Embodiment 27, wherein the omega 3 fatty acid or pharmaceutically acceptable or food grade acceptable derivative thereof is provided in granular or powder form.

[Embodiment 29] A method according to Embodiment 27 or 28, wherein the omega 3 fatty acid or pharmaceutically acceptable or food grade acceptable derivative thereof wherein the omega 3 fatty acid or pharmaceutically acceptable or food grade acceptable derivative thereof is microencapsulated.

[Embodiment 30] A nutrient composition comprising:
an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*; and an effective amount of an omega 3 fatty acid or pharmaceutically acceptable or food grade acceptable derivative thereof.

[Embodiment 31] A composition according to Embodiment 30, wherein the omega 3 fatty acid or pharmaceutically acceptable or food grade acceptable derivative thereof is provided in powder form.

[Embodiment 32] A composition according to Embodiment 30 or 31, wherein the omega 3 fatty acid or pharmaceutically acceptable or food grade acceptable derivative thereof is provided in microencapsulated powder form.

[Embodiment 33] A composition according to any one of Embodiments 30, 31, and 32, wherein the nutrient composition further comprises an effective amount of an omega 6 fatty acid or pharmaceutically acceptable or food grade acceptable derivative thereof.

[Embodiment 34] A composition according to Embodiment 33, wherein the omega 6 fatty acid is selected from GLA and DGLA, or pharmaceutically acceptable or food grade acceptable derivative thereof.

[Embodiment 35] A method according to any one of Embodiments 1, 2, 3, 4, 5, 6, 7, 8, 9, 10, 11, 12, 13, 14, 15, 16, 17, 18, 19, 20, 21, 22, 23, 24, 25, 26, 27, 28, and 29, wherein the nutrient composition further comprises an effective amount of an omega 6 fatty acid or pharmaceutically acceptable or food grade acceptable derivative thereof.

[Embodiment 36] A method according to Embodiment 35, wherein the omega 6 fatty acid is selected from GLA and DGLA, or pharmaceutically acceptable or food grade acceptable derivative thereof.

[Embodiment 37] A method enhancing cognitive function, comprising administering to a patient in need thereof a nutrient composition that enhances one or more aspects of cognition; said composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

[Embodiment 38] A method according to Embodiment 37, wherein the aspect of cognition are selected from attention, learning, and memory.

[Embodiment 39] A method according to Embodiment 37 or 38, further comprising an effective amount of an omega 3 fatty acid or pharmaceutically acceptable or food grade acceptable derivative thereof.

[Embodiment 40] A method treating stroke or an associated symptom thereof, comprising administering to a patient in need thereof a nutrient composition comprising an effective amount of a mixture or purified mixture thereof comprising three or more botanical extracts selected from the group of botanicals consisting of *gymnema sylvestre, commiphora mukul, curcuma longa, camellia sinensis, emblica officinalis*, and *terminalis chebula*.

[Embodiment 41] A method according to Embodiment 40, further comprising an effective amount of an omega 3 fatty acid or pharmaceutically acceptable or food grade acceptable derivative thereof.

[Embodiment 42] A method according to any one of Embodiments 37, 38, 39, 40, and 41, wherein the nutrient composition is in granular or powder form.

[Embodiment 43] A method according to any one of Embodiments 37, 38, 39, 40, 41, and 42, wherein the nutrient composition is capable of being administered orally.

[Embodiment 44] A method according to any one of Embodiments 37, 38, 39, 40, 41, 42, and 43, wherein the nutrient composition is combined with a liquid vehicle for oral consumption by the patient.

[Embodiment 45] A method according to Embodiment 44, wherein the liquid vehicle comprises water or milk.

[Embodiment 46] A method according to any one of Embodiments 37, 38, 39, 40, 41, 42, 43, 44, and 45, wherein the nutrient composition comprises a mixture or purified mixture thereof comprising botanical extracts selected from each of *gymnema sylvestre, commiphora mukul, curcuma longa, camellia sinensis, emblica officinalis*, and *terminalis chebula*,

[Embodiment 47] A method according to any one of Embodiments 37, 38, 39, 40, 41, 42, 43, 44, 45, and 46, wherein the nutrient composition further comprises *cinnamomum verum* or *capsicum annuum*.

[Embodiment 48] A method according to any one of Embodiments 37, 38, 39, 40, 41, 42, 43, 44, 45, 46, and 47, wherein the nutrient composition further comprises an amino acid composition comprising one or more amino acids.

[Embodiment 49] A method according to Embodiment 48, wherein the amino acid composition comprises a whey protein isolate.

[Embodiment 50] A method according to Embodiment 48 or 49, wherein the one or more amino acids contained in the amino acid composition are selected from the group consisting of: alanine, arginine, aspartic acid, cysteine, cystine, glutamic acid, glycine, histidine, isoleucine, leucine, lysine, methionine, phenylalanine, proline, serine, threonine, tryptphan, tyrosine, and valine.

[Embodiment 51] A method according to any one of Embodiments 37, 38, 39, 40, 41, 42, 43, 44, 45, 46, 47, 48, 49, and 50, wherein the nutrient composition is gluten or casein free.

[Embodiment 52] A method according to any one of Embodiments 37, 38, 39, 40, 41, 42, 43, 44, 45, 46, 47, 48, 49, 50, and 51, wherein the nutrient composition further comprises taurine or theonine.

[Embodiment 53] A method according to 52, wherein the taurine is L-taurine and the theonine is L-theonine.

[Embodiment 54] A method according to any one of Embodiments 37, 38, 39, 40, 41, 42, 43, 44, 45, 46, 47, 48, 49, 50, 51, 52, and 53, wherein the nutrient composition further comprises at least one copper containing compound.

[Embodiment 55] A method according to Embodiment 54, wherein the copper compound containing nutrient composition further comprises at least one metal containing compound, wherein the metal is selected from the group consisting of calcium, magnesium, zinc, selenium, manganese, chromium, and molybdenum.

[Embodiment 56] A method according to any one of Embodiments 37, 38, 39, 40, 41, 42, 43, 44, 45, 46, 47, 48, 49, 50, 51, 52, 53, 54, and 55, wherein the nutrient composition further comprises at least one vitamin.

[Embodiment 57] A method according to any one of Embodiments 37, 38, 39, 40, 41, 42, 43, 44, 45, 46, 47, 48, 49, 50, 51, 52, 53, 54, 55, and 56, wherein the at least one vitamin is selected from the group consisting of vitamin A, vitamin B-1 (thiamine), vitamin B-2 (riboflavin), vitamin B-3 (niacin), vitamin B-5 (pantothenic acid), vitamin B-6, vitamin B-7 (biotin), vitamin B-9 (folic acid), vitamin B-12, vitamin C, vitamin D-3, and vitamin E.

[Embodiment 58] A method according to any one of Embodiments 37, 38, 39, 40, 41, 42, 43, 44, 45, 46, 47, 48, 49, 50, 51, 52, 53, 54, 55, 56, and 57, wherein the nutrient composition further comprises at least one protein source.

[Embodiment 59] A method according to 58, wherein the at least one protein source comprises brown rice powder.

[Embodiment 60] A method according to any one of Embodiments 37, 38, 39, 40, 41, 42, 43, 44, 45, 46, 47, 48, 49, 50, 51, 52, 53, 54, 55, 56, 57, 58, and 59, wherein the nutrient composition further comprises at least one source of sugars, dietary fiber, or other carbohydrate.

[Embodiment 61] A method according to Embodiment 57, wherein the one or more vitamins in an administered dose are present in the range of:
  from about 2000 IU to about 3000 IU of vitamin A;
  from about 1 mg to about 2 mg of vitamin B-1;
  from about 1 mg to about 2 mg of vitamin B-2;
  from about 10 mg to about 30 mg of vitamin B-3;
  from about 5 mg to about 15 mg of vitamin B-5;
  from about 1 mg to about 3 mg of vitamin B-6;
  from about 10 mcg to about 50 mcg of vitamin B-7;
  from about 200 mcg to about 600 mcg of vitamin B-9;
  from about 2 mcg to about 10 mcg of vitamin B-12;
  from about 30 mg to about 90 mg of vitamin C;
  from about 200 IU to about 600 IU of vitamin D-3; and
  from about 10 IU to about 50 IU of vitamin E.

[Embodiment 62] A method according to any one of Embodiments 37, 38, 39, 40, 41, 42, 43, 44, 45, 46, 47, 48, 49, 50, 51, 52, 53, 54, 55, 56, 57, 58, 59, 60, and 61, wherein the nutrient composition further comprises iodine.

[Embodiment 63] A method according to any one of Embodiments 37, 38, 39, 40, 41, 42, 43, 44, 45, 46, 47, 48, 49, 50, 51, 52, 53, 54, 55, 56, 57, 58, 59, 60, 61, and 62, wherein the nutrient composition further comprises (a) whey protein isolate, L-taurine, L-theonine, vitamin A (as retinol palmitate), vitamin B-1 (as thiamine mononitrate), vitamin B-2 (as riboflavin), vitamin B-3 (as niacinamide), vitamin B-5 (as d-ca pantothenate), vitamin B-6 (as pyridoxine HCl), vitamin B-7 (as biotin), vitamin B-9 (as folic acid), vitamin B-12 (as cyanocobalamin), vitamin C (as ascorbic acid), vitamin D-3 (as cholecalciferol), and vitamin E (as d-alpha tocopherol), brown rice powder, sugar, apple fiber, cocoa powder, xanthan gum, potassium gluconate, calcium lactate, stevia, iodine yeast, chromium yeast, manganese yeast, zinc gluconate, selenium yeast, magnesium oxide, copper gluconate, and molybdenum yeast, and (b) cocoa flavor and *capsicum annuum*; or vanilla flavor and *cinnamomum verum*.

[Embodiment 64] A method according to any one of Embodiments 37, 38, 39, 40, 41, 42, 43, 44, 45, 46, 47, 48, 49, 50, 51, 52, 53, 54, 55, 56, 57, 58, 59, 60, 61, 62, and 63, further comprising an effective amount of an omega 3 fatty acid or pharmaceutically acceptable or food grade acceptable derivative thereof.

[Embodiment 65] A method according to Embodiment 64, wherein the omega 3 fatty acid or pharmaceutically acceptable or food grade acceptable derivative thereof is provided in granular or powder form.

[Embodiment 66] A method according to Embodiment 64 or 65, wherein the omega 3 fatty acid or pharmaceutically acceptable or food grade acceptable derivative thereof wherein the omega 3 fatty acid or pharmaceutically acceptable or food grade acceptable derivative thereof is microencapsulated.

[Embodiment 67] A method according to any one of Embodiments 37, 38, 39, 40, 41, 42, 43, 44, 45, 46, 47, 48, 49, 50, 51, 52, 53, 54, 55, 56, 57, 58, 59, 60, 61, 62, 63, 64, 65, and 66, wherein the nutrient composition further comprises an effective amount of an omega 6 fatty acid or pharmaceutically acceptable or food grade acceptable derivative thereof.

[Embodiment 68] A method according to Embodiment 67, wherein the omega 6 fatty acid is selected from GLA and DGLA, or pharmaceutically acceptable or food grade acceptable derivative thereof.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for treating apraxia, autism, speech impairments, traumatic brain injury, seizure disorders, epilepsy, global delays, or ADHD, comprising administering to a patient in need thereof a nutrient composition that ameliorates one or more symptoms of apraxia, autism, speech impairments, traumatic brain injury, seizure disorders, epilepsy, global delays, or ADHD, said nutrient composition comprising an effective amount of a mixture or purified mixture thereof comprising botanical extracts selected from each of the group of botanicals consisting of *gymnema sylvestre, commiphora mukul, curcuma longa, camellia sinensis, emblica officinalis*, and *terminalia chebula*.

2. A method according to claim 1, wherein the nutrient composition is in granular or powder form.

3. A method according to claim 2, wherein the nutrient composition is capable of being administered orally.

4. A method according to claim 3, wherein the nutrient composition is combined with a liquid vehicle for oral consumption by the patient.

5. A method according to claim 4, wherein the liquid vehicle comprises water or milk.

6. A method according to claim 1, wherein the nutrient composition further comprises *cinnamomum verum* or *capsicum annuum*.

7. A method according to claim 1, wherein the composition further comprises an amino acid composition comprising one or more amino acids.

8. A method according to claim 7, wherein the amino acid composition comprises a whey protein isolate.

9. A method according to claim 7, wherein the one or more amino acids contained in the amino acid composition are selected from the group consisting of: alanine, arginine, aspartic acid, cysteine, cystine, glutamic acid, glycine, histidine, isoleucine, leucine, lysine, methionine, phenylalanine, proline, serine, threonine, tryptphan, tyrosine, and valine.

10. A method according to claim 1, wherein the nutrient composition is gluten or casein free.

11. A method according to claim 9, wherein the nutrient composition further comprises taurine or theonine.

12. A method according to claim 11, wherein the taurine is L-taurine and the theonine is L-theonine.

13. A method according to claim 1, wherein the nutrient composition further comprises at least one copper containing compound.

14. A method according to claim 13, wherein the copper compound containing nutrient composition further comprises at least one metal containing compound, wherein the metal is selected from the group consisting of calcium, magnesium, zinc, selenium, manganese, chromium, and molybdenum.

15. A method according to claim 1, wherein the nutrient composition further comprises at least one vitamin.

16. A method according to claim 15, wherein the at least one vitamin is selected from the group consisting of vitamin A, vitamin B-1, vitamin B-2, vitamin B-3, vitamin B-5, vitamin B-6, vitamin B-7, vitamin B-9, vitamin B-12, vitamin C, vitamin D-3, and vitamin E.

17. A method according to claim 1, wherein the nutrient composition further comprises at least one protein source.

18. A method according to claim 17, wherein the at least one protein source comprises brown rice powder.

19. A method according to claim 1, wherein the nutrient composition further comprises at least one source of sugars, dietary fiber, or other carbohydrate.

20. A method according to claim 16, wherein the one or more vitamins in an administered dose are present in the range of:
from about 2000 IU to about 3000 IU of vitamin A;
from about 1 mg to about 2 mg of vitamin B-1;
from about 1 mg to about 2 mg of vitamin B-2;
from about 10 mg to about 30 mg of vitamin B-3;
from about 5 mg to about 15 mg of vitamin B-5;
from about 1 mg to about 3 mg of vitamin B-6;
from about 10 mcg to about 50 mcg of vitamin B-7;
from about 200 mcg to about 600 mcg of vitamin B-9;
from about 2 mcg to about 10 mcg of vitamin B-12;
from about 30 mg to about 90 mg of vitamin C;
from about 200 IU to about 600 IU of vitamin D-3; and
from about 10 IU to about 50 IU of vitamin E.

21. A method according to claim 1, wherein the nutrient composition further comprises iodine.

22. A method according to claim 1, wherein the nutrient composition further comprises
(a) whey protein isolate, L-taurine, L-theonine, vitamin A, vitamin B-1, vitamin B-2, vitamin B-3, vitamin B-5, vitamin B-6, vitamin B-7, vitamin B-9, vitamin B-12, vitamin C, vitamin D-3, and vitamin E, brown rice powder, sugar, apple fiber, cocoa powder, xanthan gum, potassium gluconate, calcium lactate, stevia, iodine yeast, chromium yeast, manganese yeast, zinc gluconate, selenium yeast, magnesium oxide, copper gluconate, and molybdenum yeast, and
(b) cocoa flavor and *capsicum annuum*; or
vanilla flavor and *cinnamomum verum*.

23. A method for treating apraxia, autism, speech impairments, traumatic brain injury, seizure disorders, epilepsy, global delays, Alzheimer's Disease, or ADHD comprising administering to a patient in need thereof a nutrient composition that ameliorates one or more symptoms of apraxia, autism, speech impairments, traumatic brain injury, seizure disorders, epilepsy, global delays, Alzheimer's Disease, or ADHD, said nutrient composition comprising an effective amount of a mixture or purified mixture thereof comprising botanical extracts selected from each of the group of botanicals consisting of *gymnema sylvestre, commiphora mukul, curcuma longa, camellia sinensis, emblica officinalis*, and *terminalia chebula*.

24. A method for treating stroke or an associated symptom thereof comprising administering to a patient in need thereof a nutrient composition that ameliorates one or more symptoms of stroke, said nutrient composition comprising an effective amount of a mixture or purified mixture thereof comprising each of the botanical extracts selected from the group of botanicals consisting of *gymnema sylvestre, commiphora mukul, curcuma longa, camellia sinensis, emblica officinalis*, and *terminalia chebula*.

25. A method for enhancing cognitive function comprising administering to a patient in need thereof a nutrient composition that enhances one or more aspects of cognition, said nutrient composition comprising an effective amount of a mixture or purified mixture thereof comprising each of the botanical extracts selected from the group of botanicals consisting of *gymnema sylvestre, commiphora mukul, curcuma longa, camellia sinensis, emblica officinalis*, and *terminalia chebula*.

26. A method according to claim 25, wherein the patient is suffering cognitive dysfunction.

27. A method according to claim 26, wherein the cognitive dysfunction is associated with condition or disorder selected from the group consisting of: Alzheimer's Disease, mild cognitive impairment, age-related cognitive decline, vascular dementia, Parkinson's Disease dementia, amyotrophic lateral sclerosis, Huntington's Disease, stroke, traumatic brain injury, AIDS-associated dementia, schizophrenia, Lewy-body variant of Alzheimer's Disease with or without association with Parkinson's Disease, Creutzfeld-Jakob Disease, Korsakoff's Disorder, learning disabilities caused by degenerative disorders, learning disabilities caused by non-degenerative disorders, genetic conditions, cerebral senility, vascular dementia, electric shock induced amnesia, memory impairment associated with depression or anxiety, memory impairment associated with surgical procedures including coronary artery bypass grafting, Down's syndrome, and combinations thereof.

28. A method according to claim 26, wherein the cognitive dysfunction comprises memory loss.

29. A method according to claim 25, wherein the aspect of cognition is selected from attention, learning and memory.

* * * * *